(12) United States Patent
Hatakeyama et al.

(10) Patent No.: US 11,193,003 B2
(45) Date of Patent: Dec. 7, 2021

(54) STRETCHABLE FILM, METHOD FOR FORMING THE SAME, STRETCHABLE WIRING FILM, AND METHOD FOR MANUFACTURING THE SAME

(71) Applicant: SHIN-ETSU CHEMICAL CO., LTD., Tokyo (JP)

(72) Inventors: Jun Hatakeyama, Jyoetsu (JP); Motoaki Iwabuchi, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 153 days.

(21) Appl. No.: 15/782,374

(22) Filed: Oct. 12, 2017

(65) Prior Publication Data
US 2018/0118915 A1    May 3, 2018

(30) Foreign Application Priority Data

Nov. 2, 2016    (JP) .............................. JP2016-214955

(51) Int. Cl.
*C08K 3/34*    (2006.01)
*A61B 5/00*    (2006.01)
(Continued)

(52) U.S. Cl.
CPC .............. *C08K 3/34* (2013.01); *A61B 5/6801* (2013.01); *C01B 33/24* (2013.01); *C08F 18/02* (2013.01);
(Continued)

(58) Field of Classification Search
CPC .......... C08L 83/06; C08L 33/00; C08L 75/00; C08L 83/04; C08F 18/02; C08G 77/20;
(Continued)

(56) References Cited

U.S. PATENT DOCUMENTS 4,889,901 A * 12/1989 Shama .................... C09D 4/00
526/279
5,104,929 A * 4/1992 Bilkadi ................... C08J 7/047
524/847
(Continued)

FOREIGN PATENT DOCUMENTS

JP    H5-278166 A    10/1993
JP    2004-033468 A    2/2004
(Continued)

OTHER PUBLICATIONS

Aug. 25, 2020 Office Action issued in Japanese Patent Application No. 2017-189512.

*Primary Examiner* — Ling Siu Choi
*Assistant Examiner* — Ronald Grinsted
(74) *Attorney, Agent, or Firm* — Oliff PLC

(57) ABSTRACT

The present invention provides a stretchable film including: a cured product of a composition which contains (A) a (meth)acrylate compound having silsesquioxane, (B) a (meth)acrylate compound other than the component (A) having a urethane bond, and (C) an organic solvent having a boiling point in the range of 115 to 200° C. at atmospheric pressure; wherein the component (A) is localized in the direction of a surface of the film. The stretchable film of the present invention is excellent in stretchability and strength as well as repellency on the film surface.

13 Claims, 6 Drawing Sheets

(51) Int. Cl.
*C01B 33/24* (2006.01)
*C08F 18/02* (2006.01)
*C08G 77/20* (2006.01)
*C08L 83/04* (2006.01)
*C08L 83/06* (2006.01)
*A61B 5/25* (2021.01)
*A61B 5/296* (2021.01)
*C09J 7/00* (2018.01)

(52) U.S. Cl.
CPC .............. *C08G 77/20* (2013.01); *C08L 83/04* (2013.01); *C08L 83/06* (2013.01); *A61B 5/25* (2021.01); *A61B 5/296* (2021.01); *C09J 7/00* (2013.01)

(58) Field of Classification Search
CPC . C08K 3/34; C09J 7/00; A61B 5/6801; A61B 5/296; A61B 5/25; C01B 33/24
USPC ........................................................... 524/80
See application file for complete search history.

(56) References Cited

U.S. PATENT DOCUMENTS

| 10,513,586 | B2* | 12/2019 | Kondo | C08F 2/50 |
| 2010/0003493 | A1* | 1/2010 | Cheng | C08F 220/36 |
| | | | | 428/220 |
| 2011/0048261 | A1 | 3/2011 | Shimura | |
| 2015/0004406 | A1 | 1/2015 | Suzuki et al. | |
| 2017/0204290 | A1* | 7/2017 | Simoff | C08G 77/20 |
| 2018/0086882 | A1 | 3/2018 | Kondo et al. | |

FOREIGN PATENT DOCUMENTS

| JP | 2005-320418 | * | 11/2005 |
| JP | 2005-320418 A | | 11/2005 |
| JP | 3865622 B2 | | 1/2007 |
| JP | 2011-194757 A | | 10/2011 |
| JP | 2013-139534 A | | 7/2013 |
| JP | 5495799 B2 | | 5/2014 |
| WO | 2016/159023 A1 | | 10/2016 |

* cited by examiner

STRETCHABLE FILM, METHOD FOR FORMING THE SAME, STRETCHABLE WIRING FILM, AND METHOD FOR MANUFACTURING THE SAME

TECHNICAL FIELD

The present invention relates to a stretchable film that combine stretchability, strength, and repellency, and a method for forming the same; as well as a stretchable wiring film in which the both sides of the conductive wiring are coated with the stretchable films, and a method for manufacturing the same.

BACKGROUND ART

In recent years, wearable devices have been developed progressively with the spread of Internet of Things (IoT). Representative examples thereof include a watch and glasses that can be connected with internet. Wearable devices that can always monitor physical conditions are also necessary in a medical field and a sports field, and are expected to be a growth field in the future.

Wearable devices include a form that is adhered to a body to monitor physical conditions constantly. Such a wearable device is generally composed of a bio-electrode to detect electric signals from a body, wiring to send the electric signals to a sensor, a semiconductor chip to be the sensor, and a battery. Normally, an adhesive pad is necessary to be adhered to skin. The structures of a bio-electrode, wiring around the same, and an adhesive pad are specifically described in Patent Document 1. In the wearable device described in Patent Document 1, a silicone based adhesive film is disposed around the bio-electrode, and the bio-electrode is connected with a sensor device by stretchable silver wiring in the shape of bellows coated with a stretchable urethane film.

Urethane films have high stretchability and strength to possess excellent mechanical properties as coating films for stretchable wiring. The urethane film, however, has hydrolytic properties to cause degradation, thereby inducing a disadvantage of lowering the stretchability and the strength due to hydrolysis. On the other hand, silicone films are free from hydrolytic properties, but has a disadvantage of lower strength.

Accordingly, it has been conducted to investigate silicone-urethane polymers with each molecule having both of a urethane bond and a siloxane bond. The cured product of this polymer has higher strength than single silicone, and lower hydrolytic properties than single polyurethane. The cured product of this polymer, however, fails to equal the strength of single polyurethane and the repellency of single silicone, only giving strength and repellency in the middle of those of silicone and polyurethane.

On the other hand, a material in which polyurethane and silicone are blended has been investigated. For example, Patent Document 2 and Patent Document 3 describe a material in which non-reactive silicone and crosslinkable polyurethane are blended. In a film formed from such a material, silicone comes up to the surface of a cured polyurethane film (bleed out) to improve the repellency of the film surface. In such a film, however, the silicone is not crosslinked, which causes peeling of silicone on the film surface to be tend to lower the repellency.

Patent Document 4 describes a material that contains crosslinkable urethane-acrylate and silicone-acrylate are blended. This material can improve the heat resistance by blending silicone-acrylate, and can form a cured product with higher strength and adhesiveness by blending urethane-acrylate. In this material, however, a solvent is not blended. Patent Document 5 describes a material that contains crosslinkable urethane-acrylate, silicone-urethane-acrylate, and a solvent having low boiling point such as ethanol and methanol. In this material, however, the ratio of the silicone-urethane-acrylate is high relative to the ratio of the urethane-acrylate. Patent Document 6 also describes a material that contains crosslinkable urethane-acrylate and silicone-urethane-acrylate are blended. In this material, however, a solvent is not blended.

As described above, the materials in which crosslinkable urethane-acrylate and silicone-(urethane)-acrylate are blended have been investigated previously. In the cured products of these materials, however, the urethane-acrylate and the silicone-(urethane)-acrylate are cured with the both being dispersed uniformly with each other. Accordingly, they can only give intermediate strength and repellency between those of silicone and polyurethane.

Patent Document 7 describes a material in which crosslinkable urethane-acrylate, silicone-urethane-acrylate, and a crosslinkable solvent are blended. In curing of material like this, however, the crosslinkable solvent, containing a polymerizable double bond, crosslinks simultaneously with crosslinking of the urethane-acrylate and the silicone-urethane-acrylate, which cause curing with the urethane-acrylate and the silicone-urethane-acrylate being dispersed uniformly with each other. Accordingly, the cured product only gives intermediate strength and repellency between those of silicone and polyurethane. Moreover, 2-ethylhexylacrylate, which is used as the crosslinkable solvent, has a boiling point above 200° C. to cause slower evaporation rate.

PRIOR ART DOCUMENTS

Patent Documents

Patent Document 1: Japanese Unexamined Patent publication (Kokai) No. 2004-033468
Patent Document 2: Japanese Unexamined Patent publication (Kokai) No. 2011-194757
Patent Document 3: Japanese Unexamined Patent publication (Kokai) No. 2013-139534
Patent Document 4: Japanese Unexamined Patent publication (Kokai) No. 2005-320418
Patent Document 5: Japanese Patent No. 3865622
Patent Document 6: Japanese Patent No. 5495799
Patent Document 7: Japanese Unexamined Patent publication (Kokai) No. H05-278166

SUMMARY OF INVENTION

Technical Problem

In view of these backgrounds, it has been demanded for developing a stretchable film that has excellent stretchability and strength equal to those of polyurethane, with the film surface having excellent repellency equal to that of silicone, and a method for forming the same.

The present invention has been accomplished to solve the foregoing problems, and an object thereof is to provide a stretchable film that has excellent stretchability and strength, with the film surface having excellent repellency, and a method for forming the same. It is also an object of the present invention to provide a stretchable wiring film using such a stretchable film, and a method for manufacturing the same.

Solution to Problem

To solve the problems, the present invention provides a stretchable film comprising:

a cured product of a composition which contains (A) a (meth)acrylate compound having silsesquioxane, (B) a (meth)acrylate compound other than the component (A) having a urethane bond, and (C) an organic solvent having a boiling point in the range of 115 to 200° C. at atmospheric pressure;

wherein the component (A) is localized in the direction of a surface of the film.

The foregoing can be a stretchable film that has excellent stretchability and strength, with the film surface having excellent repellency.

The ratio of the component (A) is preferably in the range of 0.1 to 35% by mass based on the total mass of solid contents in the composition excluding the component (C).

When the component (A) is in such a range, it is possible to localize sufficient amount of the component (A) in the direction of a surface of the stretchable film to make the repellency on the surface of the stretchable film more preferable. Since the amount of the component (A) is appropriate, and the ratio of the component (B) is not too low, the stretchable film comes to have more preferable strength and is also free from the risk of generating agglomerates of the component (A) to cause a layer separation structure with a mottled pattern.

It is preferable that the component (A) be a compound shown by the following general formula (1):

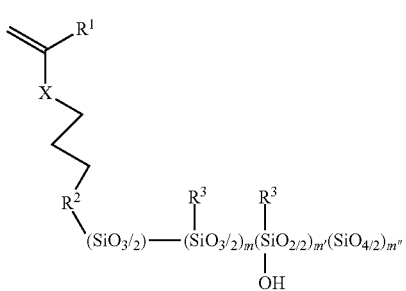

wherein $R^1$ represents a hydrogen atom or a methyl group; $R^2$ represents a single bond or a linking group shown by the following general formula (2); each $R^3$ is the same or different, and represents a hydrogen atom, a hydroxy group, a linear, branched, or cyclic hydrocarbon group having 1 to 10 carbon atoms, or a fluorinated alkyl group, optionally containing an ether group, a lactone group, an ester group, a hydroxy group, or a cyano group; X represents an ester group or $-C(=O)-O-R^7-$; $R^7$ represents a linear, branched, or cyclic alkylene group having 1 to 14 carbon atoms, a linear, branched, or cyclic alkenylene group or alkynylene group having 2 to 14 carbon atoms, or an arylene group having 6 to 10 carbon atoms, optionally having an ether group or an ester group; "m" is an integer of 4 to 40, "m'" is 0 or 1, "m''" is an integer of 0 to 8; and a part of a siloxane bond in the $(R^3-SiO_{3/2})_m$ unit is optionally cut to form a silanol group;

wherein $R^4$ and $R^5$ each independently represent a linear, branched, or cyclic alkyl group having 1 to 10 carbon atoms; $R^6$ represents a single bond, an oxygen atom, or an alkylene group having 1 to 4 carbon atoms; and "n" is an integer of 1 to 40.

Such a component (A) further improves the surface of the stretchable film in repellency and hardness.

It is preferable that the component (B) be a compound shown by the following general formula (3):

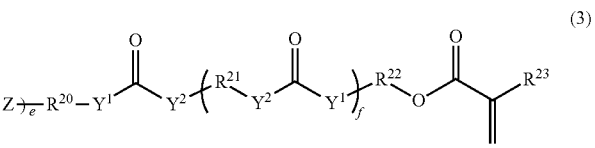

wherein $R^{23}$ represents a hydrogen atom or a methyl group; $R^{20}$ and $R^{22}$ each independently represent a single bond, a linear, branched, or cyclic alkylene group having 1 to 20 carbon atoms, an arylene group having 6 to 20 carbon atoms, or an alkenylene group having 2 to 20 carbon atoms, optionally having one or more group selected from an ether group, an ester group, an aryl group, and an arylene group; $R^{21}$ represents a single bond or a divalent hydrocarbon group having 1 to 15 carbon atoms; Z represents a single bond or a divalent hydrocarbon group having 1 to 12 carbon atoms, optionally containing one or more group selected from an ether group, an ester group, and a carbonate group; one of $Y^1$ and $Y^2$ represents an oxygen atom, and the other represents a NH group; "e" is an integer of 1 to 100, "f" is an integer of 0 to 200, and "g" is an integer of 0 to 200.

Such a component (B) further improves the stretchable film in stretchability and strength.

The component (C) is preferably one or more organic solvents selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, propylene glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, and propylene glycol monoethyl ether acetate.

Such a component (C), having a boiling point in the foregoing range, is particularly suitable for the inventive stretchable film.

The stretchable film preferably has a stretching property of 40 to 600% regulated by JIS K 6251.

With such a stretching property, the stretchable film can be particularly preferably used as a coating film of a stretchable wiring.

The stretchable film is preferably used as a film for covering a conductive wiring having stretchability.

The inventive stretchable film is particularly suitable for such a use.

The present invention also provides a method for forming a stretchable film comprising:

coating a substrate with a composition which contains (A) a (meth)acrylate compound having silsesquioxane, (B) a (meth)acrylate compound other than the component (A) having a urethane bond, and (C) an organic solvent having a boiling point in the range of 115 to 200° C. at atmospheric pressure;

evaporating the component (C) by heating, while localizing the component (A) in the direction of a surface of the film; and thereafter curing the component (A) and the component (B) by heat or light irradiation.

Such a method makes it possible to easily form a stretchable film that has excellent stretchability and strength, with the film surface having excellent repellency.

It is preferable that the ratio of the component (A) be in the range of 0.1 to 35% by mass based on the total mass of solid contents in the composition excluding the component (C).

When the component (A) is set to such a range, it is possible to localize sufficient amount of the component (A) in the direction of a surface of the stretchable film to make the repellency on the surface of the stretchable film more preferable. Since the amount of the component (A) is appropriate, and the ratio of the component (B) is not too low, the stretchable film can have more preferable strength and is free from the risk of generating agglomerates of the component (A) to cause a layer separation structure with a mottled pattern.

It is also preferable that the component (A) be a compound shown by the following general formula (1):

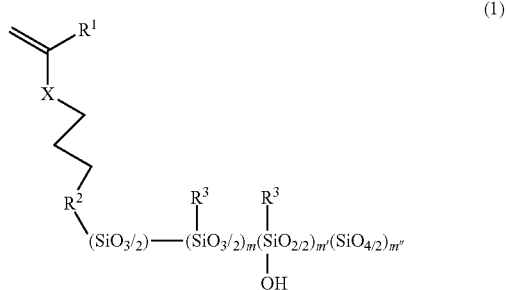

wherein $R^1$ represents a hydrogen atom or a methyl group; $R^2$ represents a single bond or a linking group shown by the following general formula (2); each $R^3$ is the same or different, and represents a hydrogen atom, a hydroxy group, a linear, branched, or cyclic hydrocarbon group having 1 to 10 carbon atoms, or a fluorinated alkyl group, optionally containing an ether group, a lactone group, an ester group, a hydroxy group, or a cyano group; X represents an ester group or —C(=O)—O—$R^7$—; $R^7$ represents a linear, branched, or cyclic alkylene group having 1 to 14 carbon atoms, a linear, branched, or cyclic alkenylene group or alkynylene group having 2 to 14 carbon atoms, or an arylene group having 6 to 10 carbon atoms, optionally having an ether group or an ester group; "m" is an integer of 4 to 40, "m'" is 0 or 1, "m''" is an integer of 0 to 8; and a part of a siloxane bond in the $(R^3—SiO_{3/2})_m$ unit is optionally cut to form a silanol group;

wherein $R^4$ and $R^5$ each independently represent a linear, branched, or cyclic alkyl group having 1 to 10 carbon atoms; $R^6$ represents a single bond, an oxygen atom, or an alkylene group having 1 to 4 carbon atoms; and "n" is an integer of 1 to 40.

By using such a component (A), it is possible to form a stretchable film that has a surface with more favorable repellency and hardness.

It is also preferable that the component (B) be a compound shown by the following general formula (3):

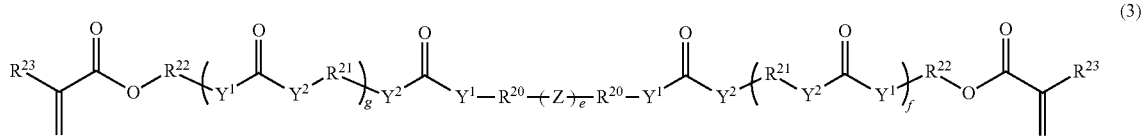

wherein $R^{23}$ represents a hydrogen atom or a methyl group; $R^{20}$ and $R^{22}$ each independently represent a single bond, a linear, branched, or cyclic alkylene group having 1 to 20 carbon atoms, an arylene group having 6 to 20 carbon atoms, or an alkenylene group having 2 to 20 carbon atoms, optionally having one or more group selected from an ether group, an ester group, an aryl group, and an arylene group; $R^{21}$ represents a single bond or a divalent hydrocarbon group having 1 to 15 carbon atoms; Z represents a single bond or a divalent hydrocarbon group having 1 to 12 carbon atoms, optionally containing one or more group selected from an ether group, an ester group, and a carbonate group; one of $Y^1$ and $Y^2$ represents an oxygen atom, and the other represents a NH group; "e" is an integer of 1 to 100, "f" is an integer of 0 to 200, and "g" is an integer of 0 to 200.

By using such a component (B), it is possible to form a stretchable film that has more favorable stretchability and strength.

As the component (C), it is preferable to use one or more organic solvents selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, propylene glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, and propylene glycol monoethyl ether acetate.

Such a component (C), having a boiling point in the foregoing range, is particularly suitable for the inventive method for forming a stretchable film.

The present invention also provides a stretchable wiring film, comprising a conductive wiring having stretchability, the both sides of the conductive wiring being coated with the stretchable film described above; wherein the surface localizing the component (A) of the stretchable film is disposed on the outside, and the conductive wiring is disposed on the inside.

The inventive stretchable wiring film described above can be a stretchable wiring film that has a surface with excellent repellency not only has excellent stretchability and strength. Accordingly, the inventive stretchable wiring film can be used suitably as a wiring unit to connect the bio-electrode and the sensor in a wearable device.

The present invention also provides a method for manufacturing the foregoing stretchable wiring film, comprising:

putting the conductive wiring having stretchability onto a substrate;

coating the substrate having the conductive wiring thereon with the composition which contains the component (A), the component (B), and the component (C);

evaporating the component (C) by heating, while localizing the component (A) in the direction of a surface of the film; and thereafter curing the component (A) and the component (B) by heat or light irradiation to form a stretchable film, thereby producing a coated wiring substrate having a single-side-coated conductive wiring;

removing the single-side-coated conductive wiring temporarily from the substrate of the coated wiring substrate;

putting the single-side-coated conductive wiring onto the substrate, with the coated side being downward;

coating the substrate having the single-side-coated conductive wiring thereon with the composition which contains the component (A), the component (B), and the component (C);

evaporating the component (C) by heating, while localizing the component (A) in the direction of a surface of the film; and thereafter curing the component (A) and the component (B) by heat or light irradiation to produce a stretchable wiring film in which both sides of the conductive wiring are coated.

Such a manufacturing method, coating the both sides of a conductive wiring with the inventive stretchable films described above, makes it possible to easily manufacture a stretchable wiring film that has a surface with excellent repellency not only has excellent stretchability and strength.

Advantageous Effects of Invention

The inventive stretchable film can be a stretchable film that has excellent stretchability and strength equal to those of polyurethane, with the film surface having excellent repellency that is equal to or more than that of linear silicone, and has higher surface hardness that have been unachievable by linear silicone. In the inventive stretchable film, (A) the (meth)acrylate compound having silsesquioxane localized in the direction of the film surface is crosslinked, which can avoid the risk of peeling of silicone on the film surface to lower the repellency unlike a film in which non-crosslinkable silicone is bled out to the surface. The silsesquioxane, which is trifunctional silicone, has extremely high hardness compared to linear siloxane, which is bifunctional. Accordingly, it is possible to improve the hardness of the film surface and the strength by localizing silsesquioxane in the direction of the surface. The inventive method for forming a stretchable film makes it possible to easily form a stretchable film that has excellent stretchability and strength equal to those of polyurethane, with the film surface having excellent repellency that is equal to that of silicone, and has higher surface hardness that have been unachievable by linear silicone. The inventive stretchable wiring film, in which the both sides of a conductive wiring are coated with such stretchable films, has a surface with excellent repellency not only has excellent stretchability and strength. Accordingly, the inventive stretchable wiring film can be particularly suitably used as a wiring unit to connect the bio-electrode and the sensor in a wearable device. The inventive manufacturing methods make it possible to easily manufacture a coated wiring substrate and a stretchable wiring film by using such a stretchable film.

DESCRIPTION OF EMBODIMENTS

Figure 1A:
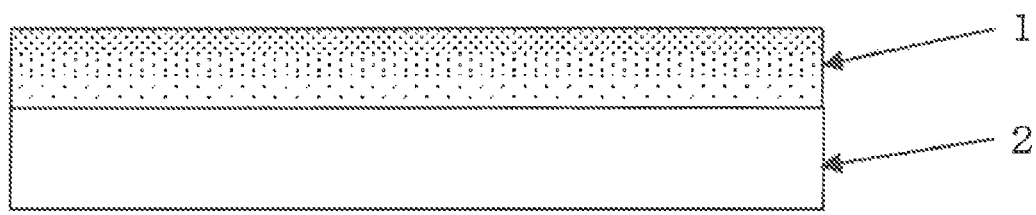
FIG. 1A is a schematic drawing showing an example of the inventive stretchable film formed on the substrate.

As described above, the polyurethane has sufficient stretchability and strength, but has a disadvantage of lower repellency to cause lowering of the strength and the stretchability due to hydrolysis; the silicone has higher repellency, but has a disadvantage of lower strength. In the cured product of silicone-urethane polymer having the both of a urethane bond and a siloxane bond, the strength and the repellency are intermediate between those of polyurethane and silicone, which fail to equal to the strength of single polyurethane and the repellency of single silicone. Even when polyurethane and silicone are blended to form a film in which the silicone is localized in the direction of the surface, the film surface still has a defect of lower strength. In view of these backgrounds, it has been demanded for developing a stretchable film that has excellent stretchability and strength equal to those of polyurethane, with the film surface having sufficient strength, together with having excellent repellency and surface hardness that are equal to or more than those of silicone, as well as a method for forming the same.

Accordingly, the present inventors have diligently investigated to solve the foregoing subject. As a result, the inventors have found that a stretchable film comprising the both of a (meth)acrylate compound having silsesquioxane with high repellency and hardness as well as a (meth)acrylate compound having a urethane bond with excellent stretchability and strength, in which the (meth)acrylate compound having silsesquioxane with excellent repellency and strength is localized in the direction of the film surface, can be a stretchable film that has excellent stretchability and strength equal to those of polyurethane, with the film surface having excellent repellency that is equal to or more than that of silicone, and having higher hardness that have been unachievable by linear silicone, and is particularly suitable as a coating film of stretchable wiring in a wearable device; thereby completing the present invention.

Here the present inventors have found that the stretchable film is effective as a stretchable film for covering a bio-electrode, having stretchability and strength equal to those of urethane-acrylate as well as high repellency, when the film is formed by coating a substrate with a composition which contains silsesquioxane resin having a polymerizable double bond(s), urethane-acrylate resin, and an organic solvent(s) having a boiling point in the range of 115 to 200° C. at atmospheric pressure; evaporating the organic solvent(s) by heating, while localizing the silsesquioxane resin having a polymerizable double bond(s) in the direction of the film surface; and thereafter curing the silsesquioxane resin having a polymerizable double bond(s) and the urethane-acrylate resin by heat or light irradiation.

That is, the present invention is a stretchable film comprising:

a cured product of a composition which contains (A) a (meth)acrylate compound having silsesquioxane, (B) a (meth)acrylate compound other than the component (A) having a urethane bond, and (C) an organic solvent having a boiling point in the range of 115 to 200° C. at atmospheric pressure;

wherein the component (A) is localized in the direction of a surface of the film.

Hereinafter, the present invention will be specifically described, but the present invention is not limited thereto.

<Stretchable Film>

The inventive stretchable film is a cured product of a composition which contains (A) a (meth)acrylate compound having silsesquioxane, (B) a (meth)acrylate compound other than the component (A) having a urethane bond, and (C) an organic solvent having a boiling point in the range of 115 to 200° C. at atmospheric pressure. Hereinafter, each component contained in the composition for forming the inventive stretchable film will be described more specifically.

[(A) (Meth)Acrylate Compound Having Silsesquioxane]

The composition for forming the inventive stretchable film contains a (meth)acrylate compound having silsesquioxane as the component (A). Herein, the (meth)acrylate compound having silsesquioxane represents a methacrylate compound having silsesquioxane or an acrylate compound having silsesquioxane. The (meth)acrylate compound having silsesquioxane also refers to a (meth)acrylate compound having a trifunctional siloxane bond(s).

Specific examples of the (meth)acrylate compound having silsesquioxane include a (meth)acrylate compound having silsesquioxane POSS (registered trade mark) (Polyhedral Oligomeric SilSesquioxanes).

The component (A) is preferably a compound(s) shown by the following general formula (1). Such a component (A) can further improve the surface of a stretchable film in repellency and hardness.

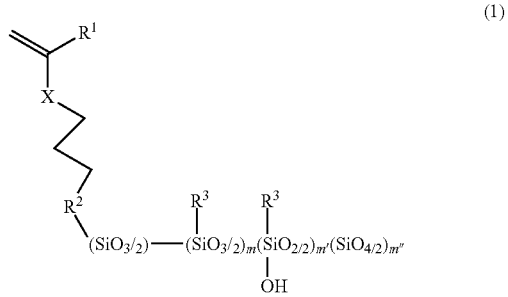

wherein $R^1$ represents a hydrogen atom or a methyl group; $R^2$ represents a single bond or a linking group shown by the following general formula (2); each $R^3$ is the same or different, and represents a hydrogen atom, a hydroxy group, a linear, branched, or cyclic hydrocarbon group having 1 to 10 carbon atoms, or a fluorinated alkyl group, optionally containing an ether group, a lactone group, an ester group, a hydroxy group, or a cyano group; X represents an ester group or —C(=O)—O—$R^7$—; $R^7$ represents a linear, branched, or cyclic alkylene group having 1 to 14 carbon atoms, a linear, branched, or cyclic alkenylene group or alkynylene group having 2 to 14 carbon atoms, or an arylene group having 6 to 10 carbon atoms, optionally having an ether group or an ester group; "m" is an integer of 4 to 40, "m'" is 0 or 1, "m''" is an integer of 0 to 8; and a part of a siloxane bond in the $(R^3—SiO_{3/2})_m$ unit is optionally cut to form a silanol group;

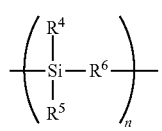

(2)

wherein $R^4$ and $R^5$ each independently represent a linear, branched, or cyclic alkyl group having 1 to 10 carbon atoms; $R^6$ represents a single bond, an oxygen atom, or an alkylene group having 1 to 4 carbon atoms; and "n" is an integer of 1 to 40.

Particularly preferable $R^3$ includes a hydrogen atom, a methyl group, an ethyl group, an n-propyl group, an isopropyl group, an n-butyl group, an isobutyl group, a 3,3,3-trifluoropropyl group, a phenyl group, a naphthyl group, a vinyl group, an allyl group, an ethynyl group, etc.

Particularly preferable $R^4$ and $R^5$ include a methyl group, an ethyl group, an n-propyl group, an isopropyl group, an n-butyl group, and an isobutyl group.

Specific examples of the compound of the general formula (1) in which the type of X is altered include the following.

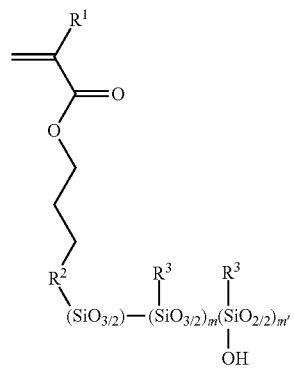

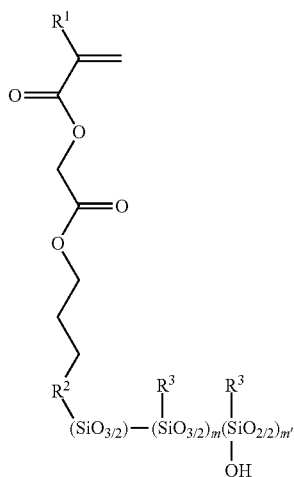

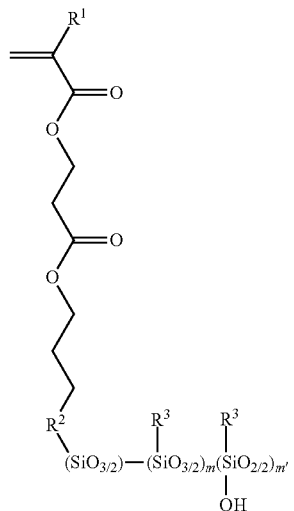

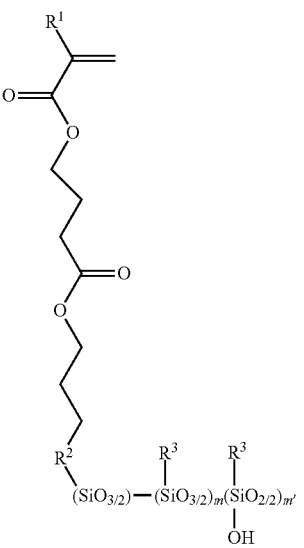

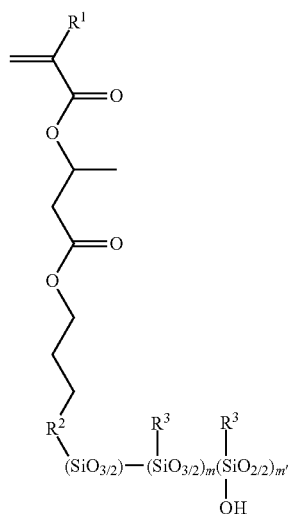

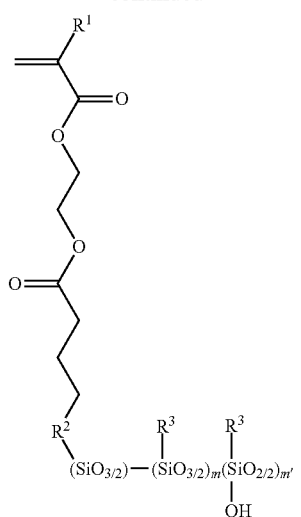
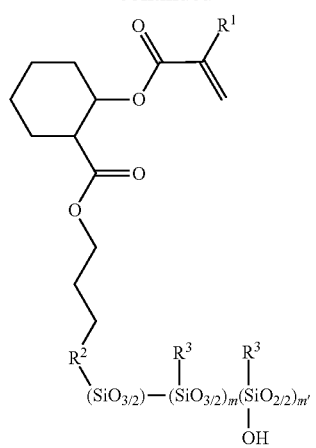
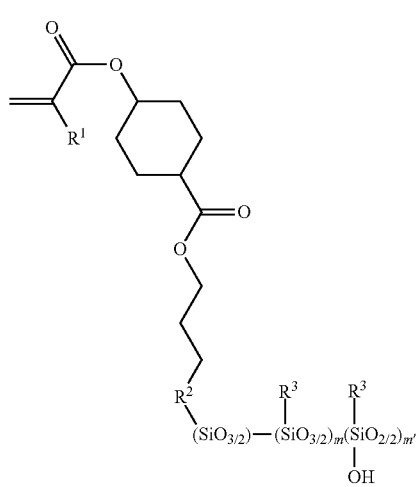
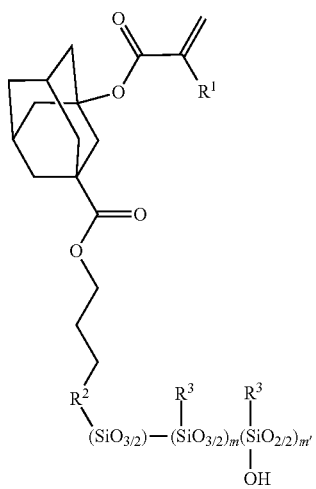
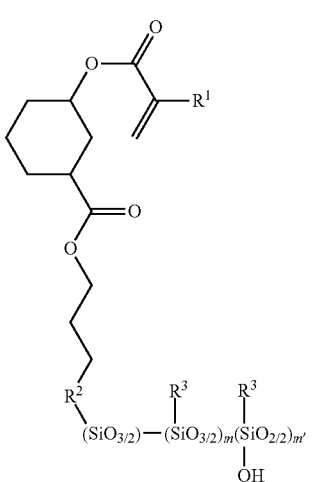
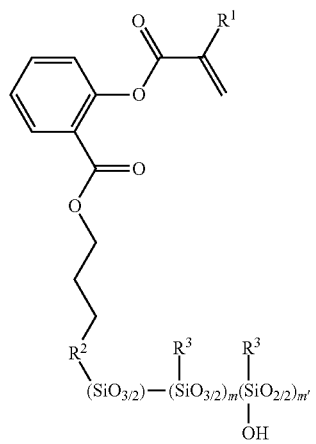

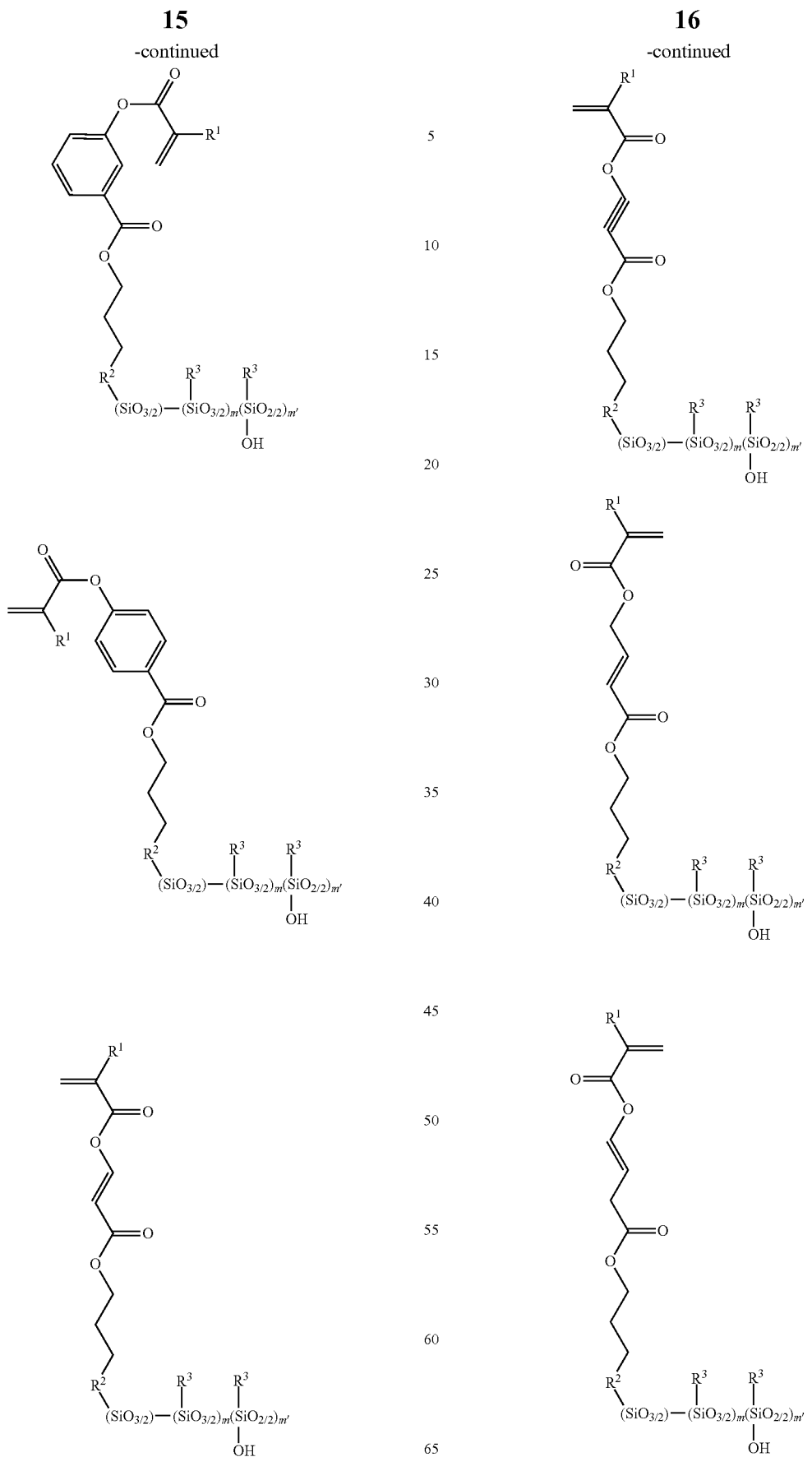

17
-continued
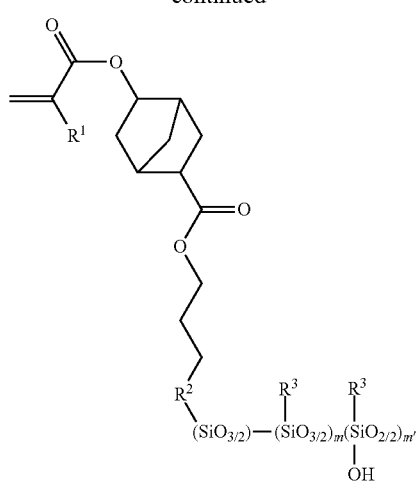
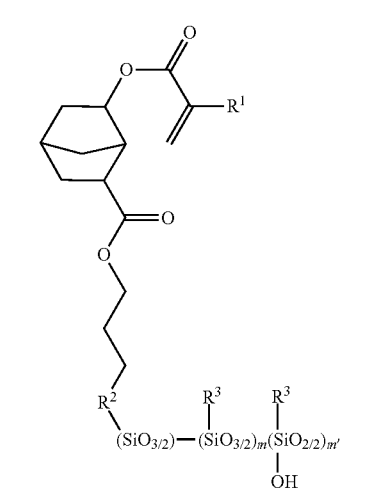
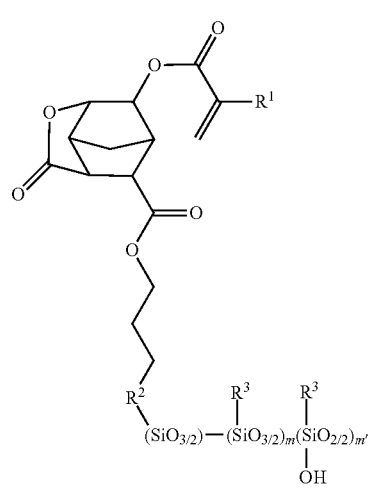
18
-continued
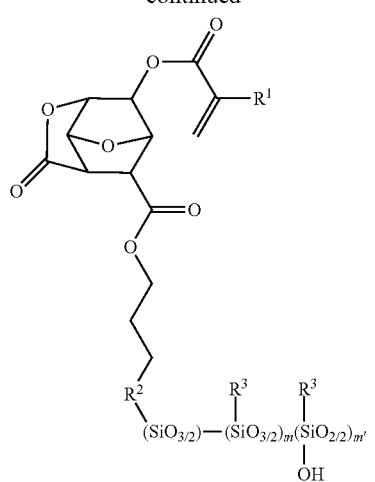
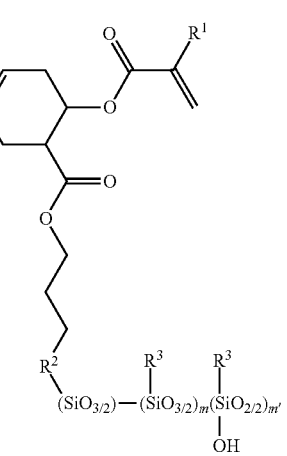
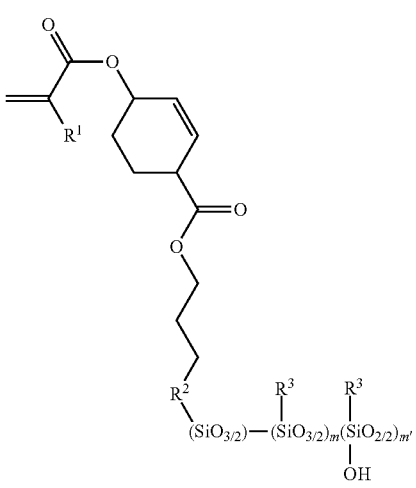

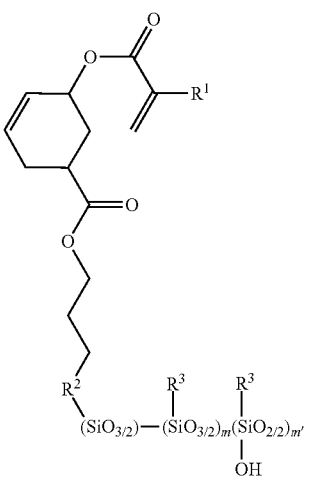

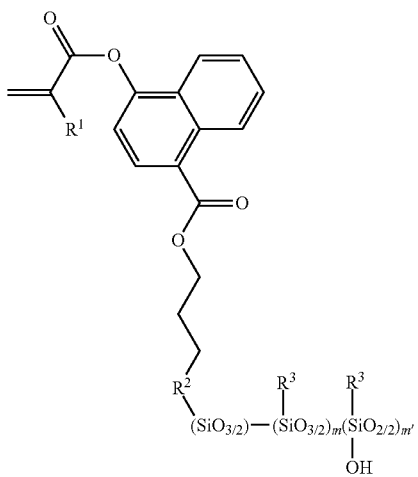

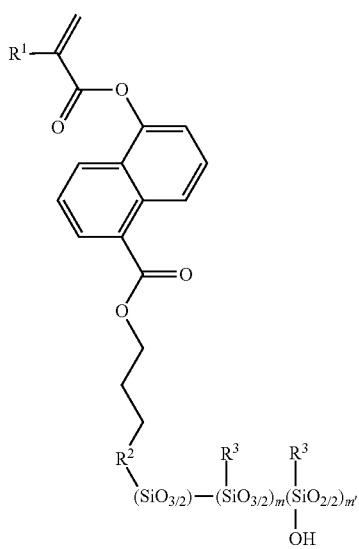

In these formulae $R^1$, $R^2$, $R^3$, "m", and "m'" have the same meanings as defined above.

Among the compounds shown by the general formula (1), silsesquioxane pendant (meth)acrylate (POSSMA) that has silsesquioxane in a three-dimensional cage structure can be synthesized by various methods including a coupling reaction of POSS-trisilanol and methacryl-pendant trichlorosilane described in Macromolecules 1995, 28, p 8435 as a representative synthesis method.

As the synthesis method of POSS-trisilanol, there has been a report of a synthesis method by a condensation reaction of cyclohexyltrichlorosilane in an aqueous acetone solution as described in J. Am. Chem. Soc. 1989, 111, p 1741. This method makes it possible to obtain POSS-trisilanol with the purity being nearly 100% by removing impurities that contain small quantities of silanol with filtration. This method, however, requires several years for improving the purity by repeating the filtration, thereby having extremely low mass-productivity.

Accordingly, a catalyst can be added to enhance the condensation rate. Illustrative examples of the catalyst to be added include acid such as acetic acid, oxalic acid, propionic acid, oleic acid, stearic acid, linoleic acid, salicylic acid, benzoic acid, formic acid, malonic acid, phthalic acid, fumaric acid, citric acid, tartaric acid, hydrochloric acid, sulfuric acid, nitric acid, sulfonic acid, methylsulfonic acid, tosic acid, and trifluoromethanesulfonic acid; base such as ammonia, sodium hydroxide, potassium hydroxide, barium hydroxide, calcium hydroxide, trimethylamine, triethylamine, triethanolamine, tetramethylammonium hydroxide, choline hydroxide, and tetrabutylammonium hydroxide; a metal chelate compound such as tetraalkoxytitan, trialkoxy mono(acetylacetonato)titan, tetraalkoxyzirconium, and trialkoxy mono(acetylacetonato)zirconium. It is also possible to raise the temperature in the range of room temperature to 100° C. to enhance the condensation rate.

The row material subjected to the condensation can be shown by the following general formula.

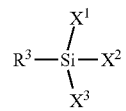

(4)

Herein, $R^3$ has the same meaning as defined above; $X^1$, $X^2$, and $X^3$ each independently represent a halogen atom, a hydroxy group, or a linear or branched alkoxy group or acyloxy group having 1 to 6 carbon atoms.

According to J. Am. Chem. Soc. 1989, 111, p 1741, condensation of a silane compound shown by the general formula (4) (particularly, cyclohexyltrichlorosilane) forms compounds shown by the following formulae (5-a), (5-b), and (5-c). Accordingly, the purity of the compound shown by the following formula (5-a) is improved by removing a compound shown by the following formula (5-b) and a compound shown by the following formula (5-c) by filtration.

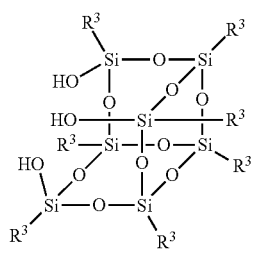
(5-a)

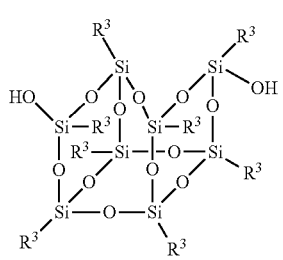
(5-b)

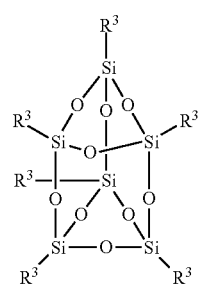
(5-c)

In these formulae, $R^3$ has the same meaning as defined above.

Subsequently, the compound shown by the formula (5-a) is coupled with a silane compound shown by the following formula (6) to give a compound shown by the following formula (7-1).

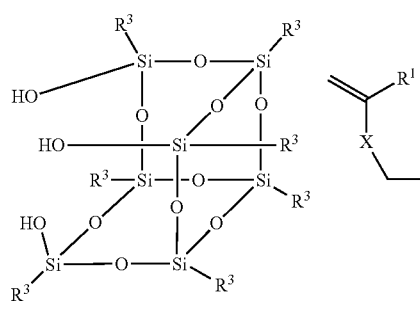

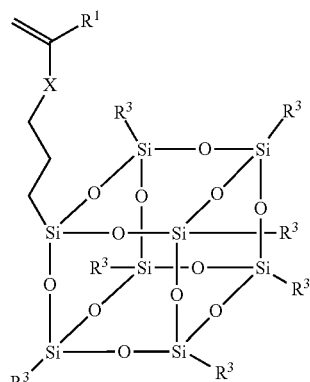
(7-1)

In these formulae, $R^1$, $R^3$, X, $X^1$, $X^2$, and $X^3$ have the same meanings as defined above.

Other synthesis methods for obtaining a compound shown by the general formula (1) include a method in which a silane compound shown by the general formula (4) and a silane compound shown by the formula (6) are mixed and subjected to co-condensation reaction. In such a manner, the compound shown by the general formula (1) can be obtained by condensation of a trifunctional silane compound.

Illustrative examples of the compound shown by the general formula (1) also include the compounds shown by the following formulae (7-2) to (7-8) other than those shown by the formula (7-1).

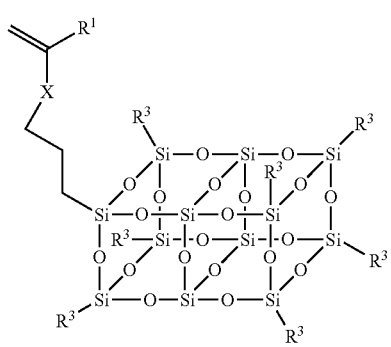
(7-2)

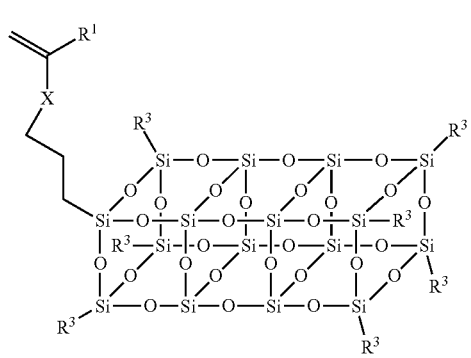
(7-3)

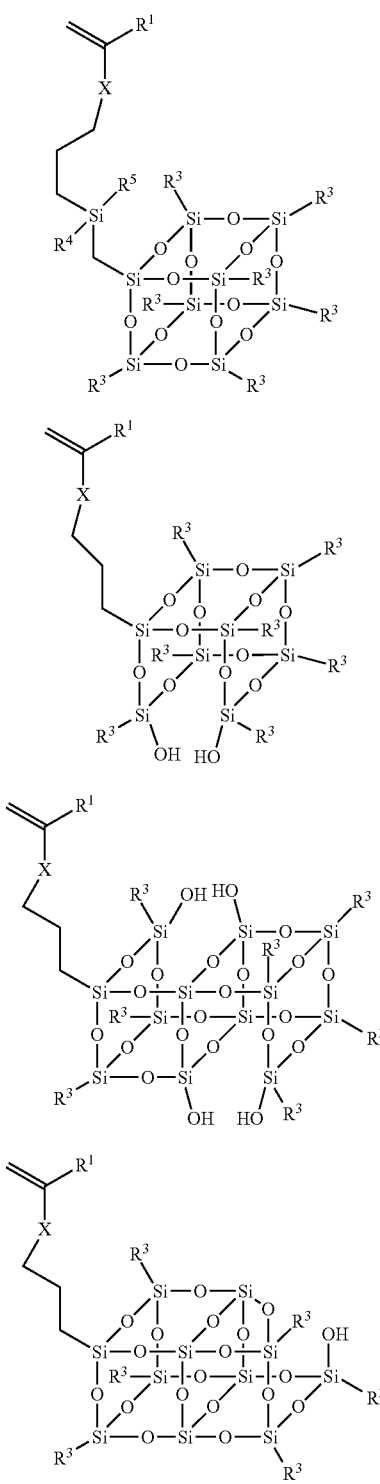

(7-4)

(7-5)

(7-6)

(7-7)

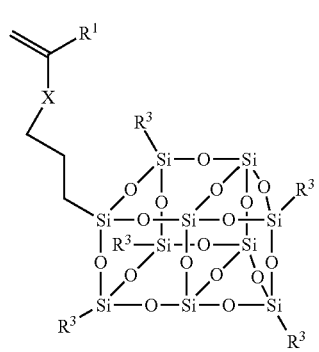

(7-8)

In these formulae, $R^1$, $R^3$, R, $R^5$, and X have the same meanings as defined above.

When the component (A) is a compound having silsesquioxane with a cage structure, the portion of the cage silsesquioxane is not necessarily a perfect cubic structure, and a part of the siloxane bonds may be cut to form a silanol. It is possible to form a cage structure in which a plurality of octahedrons are linked. The component (A) may be a compound other than that shown by the formulae (7-1) to (7-8), and may be a mixture thereof.

The ratio of the component (A) is preferably in the range of 0.1 to 35% by mass based on the total mass of solid contents in the composition excluding the component (C) that will be described below. When the component (A) is in such a range, sufficient amount of the component (A) localizes in the direction of the surface of the stretchable film, and the surface repellency of the stretchable film is further improved thereby. Additionally, the strength of the stretchable film can be more favorable, and the film is prevented from a risk of generating agglomerates of the component (A) to cause a layer separation structure with a mottled pattern since the amount of the component (A) is appropriate, and the ratio of the component (B) is not too low.

[(B) (Meth)Acrylate Compound Other than Component (A) Having Urethane Bond]

The composition for forming the inventive stretchable film contains a (meth)acrylate compound other than the component (A) having a urethane bond as the component (B). Herein, the (meth)acrylate compound having a urethane bond represents a methacrylate compound having a urethane bond or an acrylate compound having a urethane bond.

As the component (B), the compounds shown by the following general formula (3) are preferable. Such a component (B) further improves the stretchability and the strength of the stretchable film.

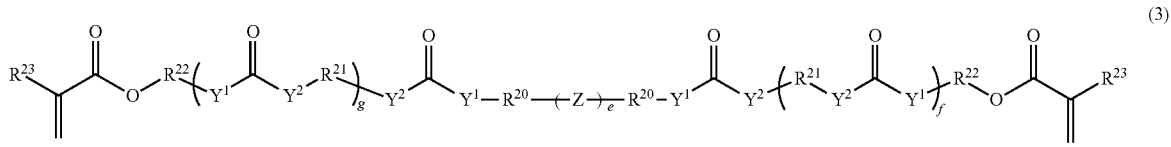

(3)

In the formula, $R^{23}$ represents a hydrogen atom or a methyl group; $R^{20}$ and $R^{22}$ each independently represent a single bond, a linear, branched, or cyclic alkylene group having 1 to 20 carbon atoms, an arylene group having 6 to 20 carbon atoms, or an alkenylene group having 2 to 20 carbon atoms, each of which may contain one or more groups selected from an ether group, an ester group, an aryl group, and an arylene group; $R^{21}$ represents a single bond or a divalent hydrocarbon group having 1 to 15 carbon atoms; Z represents a single bond, or a divalent hydrocarbon group having 1 to 12 carbon atoms, which may contain one or more groups selected from an ether group, an ester group, and a carbonate group; either $Y^1$ or $Y^2$ represents an oxygen atom, and the other represents a NH group; "e" is an integer of 1 to 100; "f" is an integer of 0 to 200; and "g" is an integer of 0 to 200.

$R^{23}$ represents a hydrogen atom or a methyl group. Incidentally, when $R^{23}$ represents a hydrogen atom, this formula represents an acrylate compound; when $R^{23}$ represents a methyl group, this formula represents a methacrylate compound.

Each of $R^{20}$ and $R^{22}$ represents a single bond, a linear, branched, or cyclic alkylene group having 1 to 20 carbon atoms, an arylene group having 6 to 20 carbon atoms, or an alkenylene group having 2 to 20 carbon atoms, each of which may contain one or more groups selected from an ether group, an ester group, an aryl group, and an arylene group. As $R^{20}$ and $R^{22}$, a methylene group, an ethylene group, a propylene group, a butylene group, and a pentylene group, etc. are particularly preferable.

$R^{21}$ represents a single bond or a divalent hydrocarbon group having 1 to 15 carbon atoms. As $R^{21}$, a methylene group, an ethylene group, a propylene group, a butylene group, and a pentylene group, etc. are particularly preferable.

Z represents a single bond, or a divalent hydrocarbon group having 1 to 12 carbon atoms which may contain one or more groups selected from an ether group, an ester group, and a carbonate group. As Z, the following groups, etc. are particularly preferable.

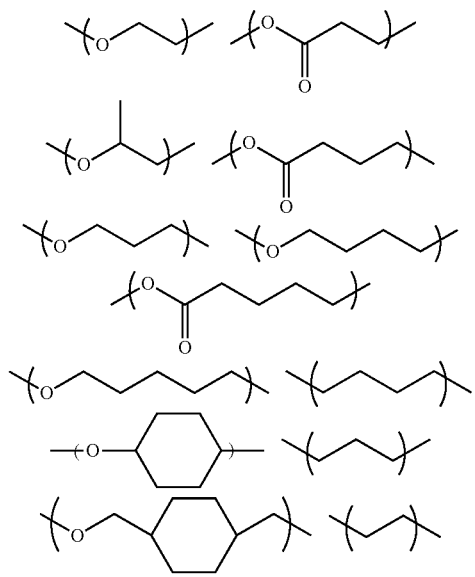

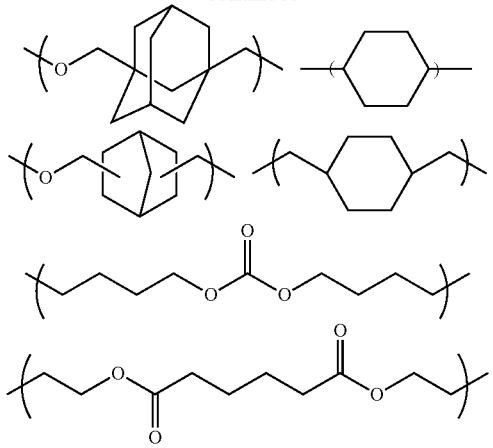

Either $Y^1$ or $Y^2$ represents an oxygen atom, and the other represents a NH group. Incidentally, this means that a pair of $Y^1$ and $Y^2$ across the carbonyl group in the formula makes this moiety be a urethane bond, with one of them being an oxygen atom and the other being an NH group.

In the foregoing formula, "e" is an integer of 1 to 100, preferably 1 to 50; "f" is an integer of 0 to 200, preferably 0 to 100; and "g" is an integer of 0 to 200, preferably 0 to 100.

The urethane-(meth)acrylate compound shown by the general formula (3) can be obtained by a method of reacting a polyether compound having hydroxy groups at the both ends with (meth)acrylate compounds each having an isocyanate group; a method of reacting a polyester compound having hydroxy groups at the both ends with (meth)acrylate compounds each having an isocyanate group; a method of reacting a polycarbonate compound having hydroxy groups at the both ends with (meth)acrylate compounds each having an isocyanate group; etc. In this case, it is also possible to use a diisocyanate compound or a dihydroxy compound as a chain extender.

As the isocyanate compounds used at this stage, the following can be exemplified.

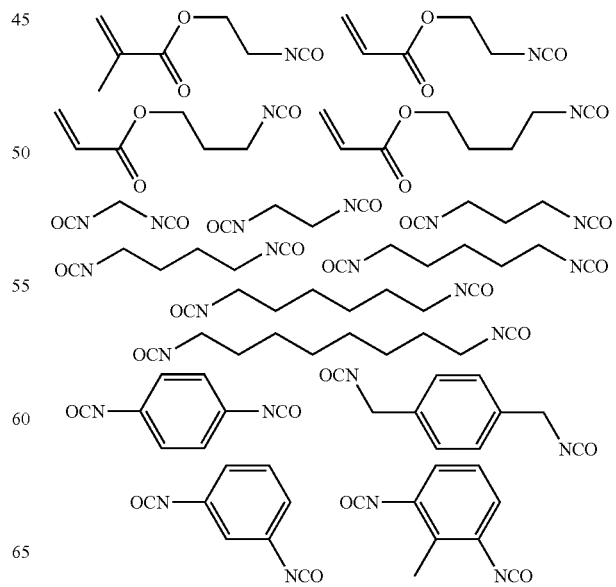

-continued

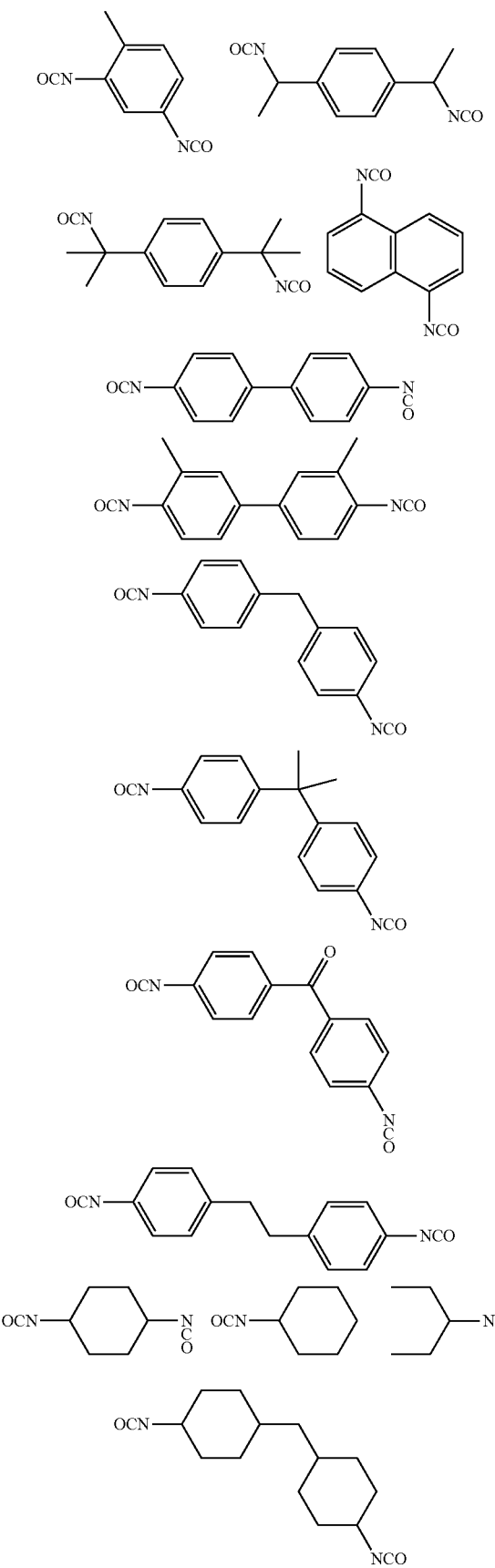

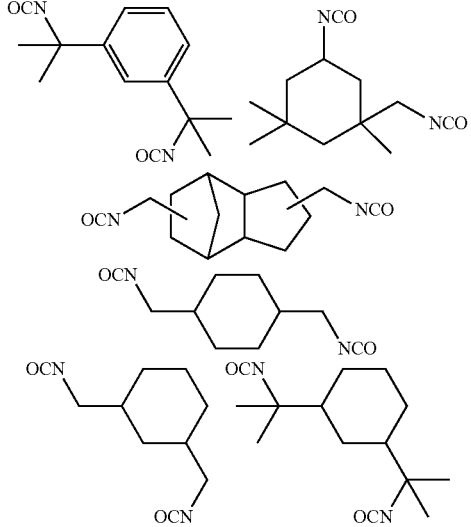

[(C) Organic Solvent Having Boiling Point in the Range of 115 to 200° C. at Atmospheric Pressure]

The composition for forming the inventive stretchable film contains an organic solvent having a boiling point in the range of 115 to 200° C. at atmospheric pressure as a component (C).

Such a component (C) is preferably one or more organic solvents specifically selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, propylene glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, and propylene glycol monoethyl ether acetate.

As will be described below, when forming the stretchable film, the component (C) is evaporated from the film surface by heating after the composition is applied on a substrate, for example. At this stage, the component (A) moves to the film surface side accompanying with moving of the component (C) to the film surface side to form a structure in which the component (A) is localized in the direction of the surface of the film. Accordingly, when the boiling point of the component (C) is below 115° C. at atmospheric pressure, the component (C) evaporates to solidify the coated film of the composition before the component (A) moves to the film surface side, which fails to localize sufficient amount of the component (A) to the film surface side. On the other hand, when the boiling point of the component (C) is above 200° C. at atmospheric pressure, the component (C) fails to evaporate sufficiently, which causes to remain a large amount of the component (C) in the stretchable film. The use of such a stretchable film as a stretchable film for a wearable device, e.g., a living body sensor, raises the risk to generate skin allergies due to gradual evaporation of the remaining solvent.

The component (C) is preferably an organic solvent without a polymerizable double bond (i.e., non crosslinkable organic solvent). Such an organic solvent can prevent crosslinking of the organic solvent having polymerizable double bond disposed on the film surface, which fails to cover the film surface with silicone-(meth)acrylate, to lower the repellency.

The amount of the component (C) to be added is preferably in the range of 5 to 1,000 parts by mass, more preferably 10 to 500 parts by mass, particularly 20 to 300 parts by mass, based on 100 parts by mass of the solid contents in the composition.

[Additives]

To cure the component (A) and the component (B), the present invention may involve addition of a radical generator, which generates a radical by light or heat. As will be described below, in the inventive method for forming a stretchable film, the component (A) is moved (localized) to the film surface side while evaporating the component (C) by heating. In this heating for evaporating the component (C), the component (A) and the component (B) may be cured. The component (A) may also be moved to the film surface by heating for evaporating the component (C), and then crosslinked by light irradiation. In the former case, a thermal-radical generator is added to the composition, and the component (A) and the component (B) are cured during the heating. In the latter case, a photo-radical generator is added to the composition, and the component (A) and the component (B) are cured by light irradiation after heating.

Illustrative examples of the thermal radical generator include an azo radical generator and a peroxide radical generator. Illustrative examples of the azo radical generator include 2,2'-azobis(isobutyronitrile) (AIBN), 2,2'-azobis(2,4-dimethylvaleronitrile), dimethyl 2,2'-azobis(2-methylpropionate), 2,2'-azobis(4-methoxy-2,4-dimethylvaleronitrile), 2,2'-azobis(cyclohexane-1-carbonitrile), and 4,4'-azobis(4-cyanovaleric acid). Illustrative examples of the peroxide radical generator include benzoyl peroxide, decanoyl peroxide, lauroyl peroxide, succinic acid peroxide, t-butyl peroxy-2-ethylhexanoate, t-butyl peroxy pivalate, and 1,1,3,3-tetramethylbutyl peroxy-2-ethylhexanoate.

Illustrative examples of the photo-radical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoic acid, 2-(1,3-benzodioxole-5-yl)-4,6-bis(trichloromethyl)-1,3,5-triazine, 2-benzyl-2-(dimethylamino)-4'-morpholinobutylophenone, 4,4'-dichlorobenzophenone, 2,2-diethoxyacetophenone, 2,2-dimethoxy-2-phenylacetophenone, 2,4-diethylthioxanthen-9-one, diphenyl(2,4,6-trimethylbenzoyl) phosphine oxide, 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, 2-phenyl-2-(p-toluenesulfonyloxy)acetophenone (BAPO), and camphorquinone.

The loading amount of the thermal radical generator or the photo-radical generator is preferably in the range of 0.1 to 50 parts by mass based on 100 parts by mass of the sum of the component (A) and the component (B).

As other additives, a thiol base crosslinking agent can be added. This makes it possible to improve the efficiency of radical crosslinking.

The inventive stretchable film is a stretchable film comprising the both of the component (A) with excellent repellency and the component (B) with excellent stretchability and strength, in which the component (A) with excellent repellency is localized in the direction of the film surface (on the one side). Such a structure allows the stretchable film to have excellent stretchability and strength equal to those of polyurethane due to the component (B), and to have a film surface with excellent repellency equals to that of silicone due to the component (A) localized in the direction of the film surface.

The inventive stretchable film preferably has a stretching property (elongation at break) of 40 to 600% regulated by JIS K 6251. With such a stretching property, the stretchable film can be particularly preferably used as a coating film of a stretchable wiring.

The inventive stretchable film is preferably used as a film for covering a conductive wiring having stretchability. The inventive stretchable film is particularly suitable for such a use.

Figure 1B:
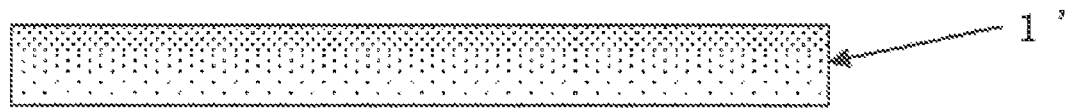
FIG. 1B is a schematic drawing showing an example of the inventive stretchable film removed (unsupported) from a substrate.

An example of the inventive stretchable film is shown in FIGS. 1A and 1B. The stretchable film 1 in FIG. 1A is formed on the substrate 2. This stretchable film 1 is a cured product of the composition containing the components (A) to (C) described above, in which the component (A) is localized in the direction of the film surface. The stretchable film 1' in FIG. 1B is the one in which the substrate 2 is removed from the stretchable film 1 formed on the substrate 2 in FIG. 1A. As described above, the inventive stretchable film may be a stretchable film formed on a substrate, etc. or may be an unsupported stretchable film. Incidentally, FIGS. 1A and 1B shows the distribution of the component (A) schematically with light and shade, in which the component (A) is localized in the direction of the film surface having darker shade.

The inventive stretchable film described above can be a stretchable film that has excellent stretchability and strength equal to those of polyurethane, with the film surface having excellent repellency equal to that of silicone and hardness that have been unachievable by linear silicone. Moreover, it is free from the risk of peeling of silicone on the film surface to lower the repellency, unlike the one having silicone bred out to the surface, because of crosslinking of (A) the (meth)acrylate compound having silsesquioxane localized in the direction of the film surface.

<Method for Forming Stretchable Film>

The present invention also provides a method for forming a stretchable film comprising:

coating a substrate with a composition which contains (A) a (meth)acrylate compound having silsesquioxane, (B) a (meth)acrylate compound other than the component (A) having a urethane bond, and (C) an organic solvent having a boiling point in the range of 115 to 200° C. at atmospheric pressure;

evaporating the component (C) by heating, while localizing the component (A) in the direction of the surface of the film; and thereafter curing the component (A) and the component (B) by heat or light irradiation.

As the composition, it is possible to use the same ones mentioned in the explanations of the stretchable film described above.

When the cured film has to be removed temporarily from the substrate later, it is preferable to use a substrate with higher release properties as the substrate, particularly a substrate on which the surface is coated with a resin having lower surface energy such as fluorine resin including Teflon (registered trade mark) and tetrafluoroethylene-perfluoroalkylvinylether copolymer (PFA), polyethylene, and polypropylene.

The method for applying the composition onto the substrate includes spin coating, bar coating, roll coating, flow coating, dip coating, spray coating, and doctor coating. The coating is preferably performed so as to have a coating film thickness of 1 µm to 2 mm.

The heating after applying the composition onto a substrate can be performed with a hot plate, in an oven, or by irradiation of far infrared ray, for example. The heating condition is preferably at 30 to 150° C. for 10 seconds to 30 minutes, more preferably 50 to 120° C. for 30 seconds to 20 minutes. The baking may be performed in any environment such as in the atmosphere, in an inert gas, or in vacuum.

Through this heating, the component (C) moves from the inside of the coating film of the composition to the direction of the film surface to evaporate out of the film surface. This causes moving of the component (A) to the direction of the film surface at this stage. When the boiling point of the component (C) is below 115° C., the component (C) is completely evaporated to solidify the coating film of the composition before the component (A) starts to move to the direction of the film surface, which lowers the ratio of the component (A) localized in the direction of the film surface. As a result, it becomes impossible to obtain sufficient repellency. On the other hand, when the boiling point of the component (C) is above 200° C., the component (C) is hard to evaporate, which makes the coating film of the composition be difficult to solidify, and not only that, the component (C) be apt to remain in the cured stretchable film in a large amount. The remaining of large amount of the component (C) has a risk of irritant to skin by gradual evaporation of the remained component (C), which is not preferable in parts of a wearable device to be in contact with skin.

It is to be noted that in case of curing the component (A) and the component (B) by heat, the component (A) and the component (B) are cured by heating for evaporating the component (C).

In case of curing the component (A) and the component (B) by light irradiation, the component (A) and the component (B) are cured by light irradiation after the foregoing heating. The light irradiation after the heating is preferably performed with a light having a wavelength of 200 to 500 nm. As the light source, a halogen lamp, a xenon lamp, excimer laser, and LED can be used, for example. Irradiation with electron beam is also preferable. The irradiation quantity is preferably in the range of 1 mJ/cm$^2$ to 100 J/cm$^2$. This gives rise to a crosslinking reaction of the component (A) and the component (B) to cure the coating film of the composition to form a stretchable film.

Figure 2A:
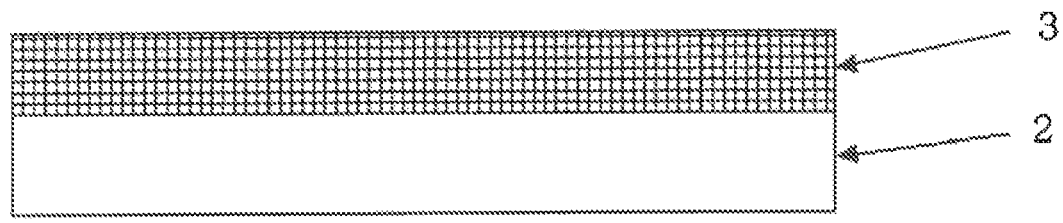
FIGS. 2A to 2D are a flow diagram showing an example of the inventive method for forming a stretchable film.
Figure 2B:
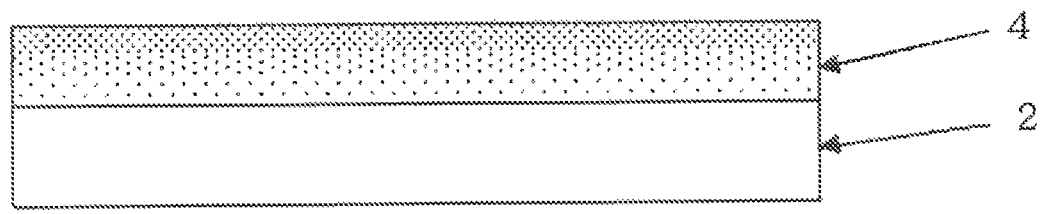
Figure 2C:
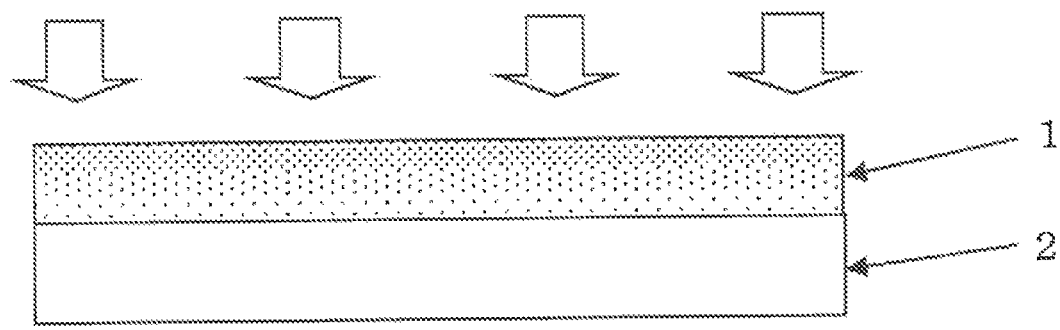
Figure 2D:
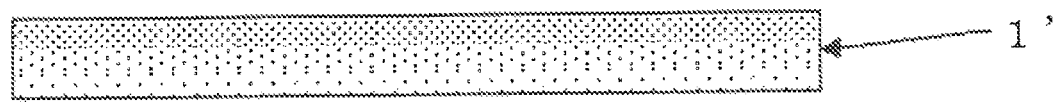

A flow diagram of an example of the inventive method for forming a stretchable film is shown in FIGS. 2A to 2D. In the method for forming a stretchable film shown in FIGS. 2A to 2D, the composition which contains the components (A) to (C) described above is applied first onto the substrate 2 to form the coating film 3 of the composition (FIG. 2A). Then, the component (C) is evaporated by heating, while localizing the component (A) in the direction of the surface of the film to form the coated film 4 in which the component (A) is localized (FIG. 2B). Subsequently, the component (A) and the component (B) are cured by light irradiation to form the stretchable film 1 (FIG. 2C). It is to be noted that the stretchable film 1 may also be removed from the substrate 2 to form the unsupported stretchable film 1' in accordance with needs (FIG. 2D).

The inventive method for forming a stretchable film described above can easily form a stretchable film that has excellent stretchability and strength equal to those of polyurethane, with the film surface having excellent repellency equal to that of silicone and higher hardness that have been unachievable by linear silicone.

<Stretchable Wiring Film>

The present invention also provides a stretchable wiring film, comprising a conductive wiring having stretchability, the both sides of the conductive wiring being coated with the inventive stretchable films described above; wherein the surface localizing the component (A) of each stretchable film is disposed on the outside, and the conductive wiring is disposed on the inside.

As the conductive wiring having stretchability, which is not particularly limited, silver wiring can be suitably used, for example.

Such a stretchable wiring film of the present invention is also excellent in repellency on the surface not only excellent in stretchability and strength. Accordingly, the inventive stretchable wiring film can be suitably used as a wiring unit to connect the bio-electrode and the sensor in a wearable device.

<Method for Manufacturing Stretchable Wiring Film>

The present invention also provides a method for manufacturing the foregoing stretchable wiring film, comprising:

putting a conductive wiring having stretchability onto a substrate;

coating the substrate having the conductive wiring thereon with the composition which contains the component (A), the component (B), and the component (C);

evaporating the component (C) by heating, while localizing the component (A) in the direction of a surface of the film; and thereafter curing the component (A) and the component (B) by heat or light irradiation to form a stretchable film, thereby producing a coated wiring substrate having a single-side-coated conductive wiring, in which one side of the conductive wiring is coated;

removing the single-side-coated conductive wiring temporarily from the substrate of the coated wiring substrate;

putting the single-side-coated conductive wiring onto the substrate, with the coated side being downward;

coating the substrate having the single-side-coated conductive wiring thereon with the composition which contains the component (A), the component (B), and the component (C);

evaporating the component (C) by heating, while localizing the component (A) in the direction of a surface of the film; and thereafter curing the component (A) and the component (B) by heat or light irradiation to produce a stretchable wiring film in which both sides of the conductive wiring are coated.

In the inventive method for manufacturing a stretchable wiring film, a coated wiring substrate having a single-side-coated conductive wiring is produced at first by putting a conductive wiring having stretchability onto a substrate; coating the substrate with a composition which contains the component (A), component (B), and component (C); evaporating the component (C) by heating, while localizing the component (A) in the direction of a surface of the film; and thereafter curing the component (A) and the component (B) by heat or light irradiation to form a stretchable film, thereby coating the single-side of the conductive wiring.

As the composition, it is possible to use the same ones mentioned in the explanation of the stretchable film described above. As the substrate, it is possible to use the same ones mentioned in the explanation of the method for forming a stretchable film described above. As the conductive wiring having stretchability, it is possible to use the same ones mentioned in the explanation of the stretchable wiring film described above.

The heating condition when evaporating the component (C) and the conditions when curing the component (A) and the component (B) by heat or light irradiation can be the same as the conditions mentioned in the explanation of the method for forming a stretchable film described above.

Figure 3A:
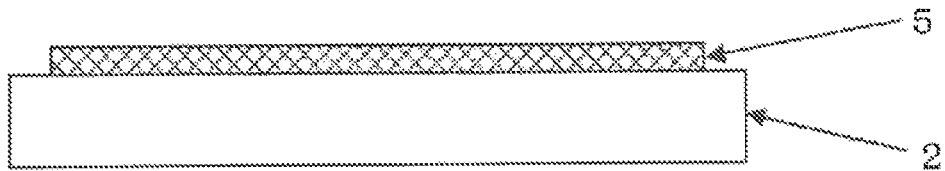
FIGS. 3A to 3E are a flow diagram showing an example of the inventive method for manufacturing a stretchable wiring film until the stage of producing a coated wiring substrate.
Figure 3B:
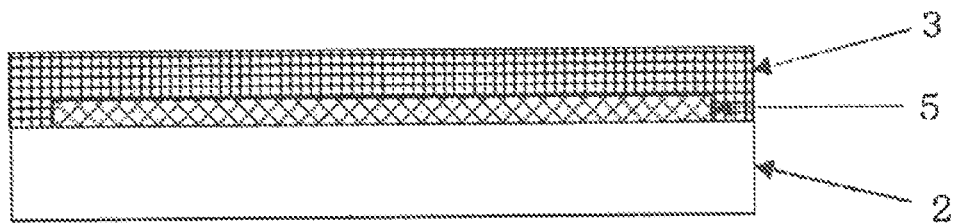
Figure 3C:
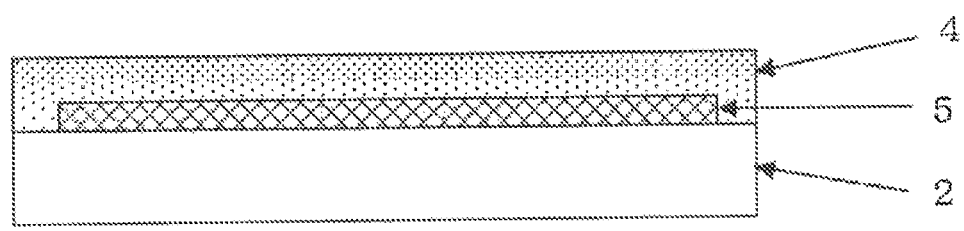
Figure 3D:
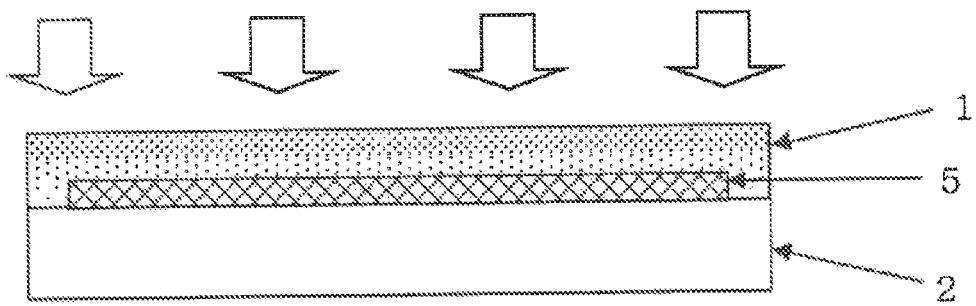
Figure 3E:
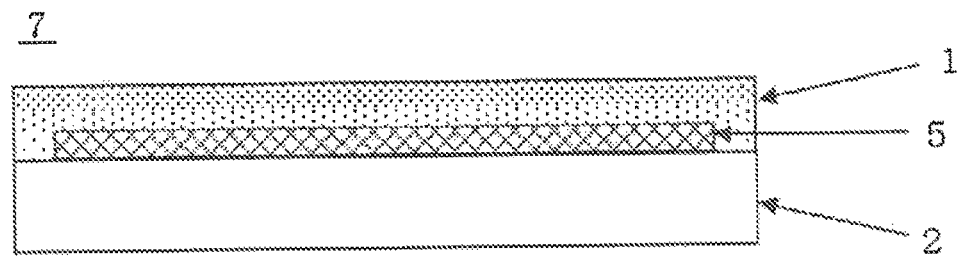

A flow diagram of FIGS. 3A to 3E shows an example of the inventive method for manufacturing a stretchable wiring film until the stage of producing a coated wiring substrate. In the method for manufacturing a stretchable wiring film shown in FIGS. 3A to 3E, the conductive wiring 5 having stretchability is put on the substrate 2 at first (FIG. 3A). Then, this is coated with the composition which contains the components (A) to (C) described above to form the coating film 3 of the composition (FIG. 3B). Subsequently, the component (C) is evaporated by heating, while localizing the component (A) in the direction of the surface of the film to form the coated film 4 in which the component (A) is localized (FIG. 3C). Then, the component (A) and the component (B) are cured by light irradiation to form the stretchable film 1 (FIG. 3D). This allows manufacturing of the coated wiring substrate 7 in which one side of the conductive wiring 5 on the substrate 2 is coated with the stretchable film 1 (FIG. 3E).

In such a manner, it is possible to easily manufacture a coated wiring substrate in which one side of the conductive wiring is coated with the inventive stretchable film, which has excellent stretchability and strength, with the film surface being excellent in repellency. The coated wiring substrate thus produced can be suitably used for the subsequent manufacturing of a stretchable wiring film.

In the inventive method for manufacturing a stretchable wiring film, a stretchable wiring film in which both sides of the conductive wiring are coated is then produced by removing the single-side-coated conductive wiring temporarily from the substrate of the coated wiring substrate produced by the foregoing method; putting the single-side-coated conductive wiring onto the substrate, with the coated side being downward; coating the substrate with a composition which contains the component (A), the component (B), and the component (C); evaporating the component (C) by heating, while localizing the component (A) in the direction of the film surface; and thereafter curing the component (A) and the component (B) by heat or light irradiation to form a stretchable film.

The composition used herein can be the same ones mentioned in the explanation of the stretchable film described above.

The heating condition when evaporating the component (C) and the conditions when curing the component (A) and the component (B) by heat or light irradiation can be the same as the conditions mentioned in the explanation of the method for forming a stretchable film described above.

Figure 4A:
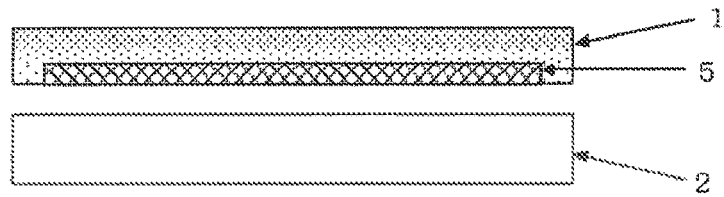
FIGS. 4A to 4F are a flow diagram showing an example of the inventive method for manufacturing a stretchable wiring film at the stages of manufacturing the stretchable wiring film from a coated wiring substrate.
Figure 4B:
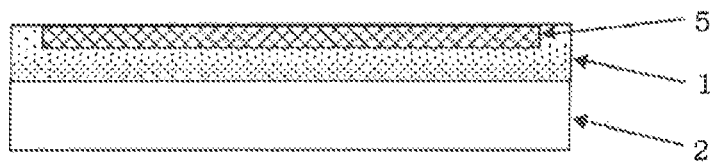
Figure 4C:
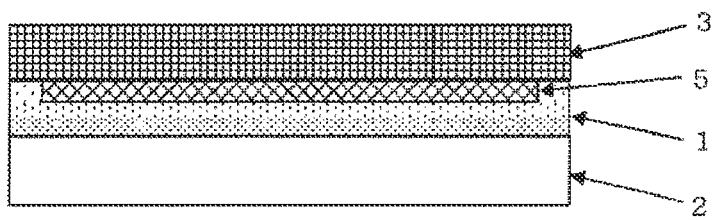
Figure 4D:
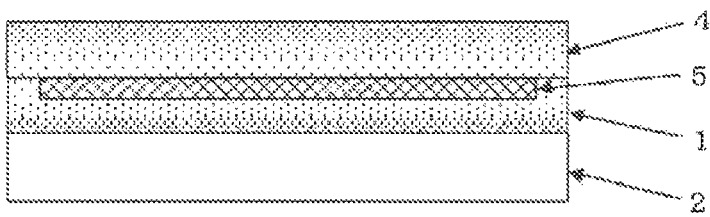
Figure 4E:
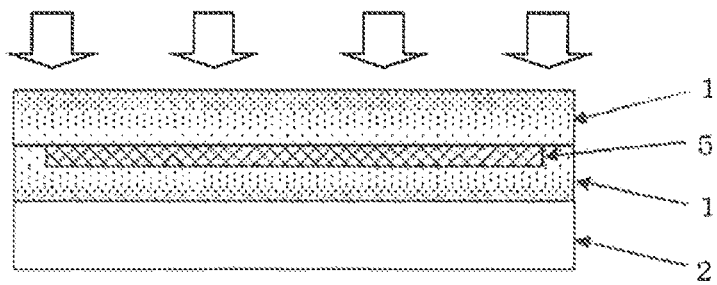
Figure 4F:
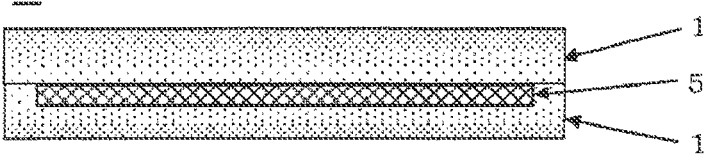

A flow diagram of FIGS. 4A to 4F shows an example of the inventive method for manufacturing a stretchable wiring film at the stages of manufacturing the stretchable wiring film from a coated wiring substrate. In the method shown in FIGS. 4A to 4F, the conductive wiring 5 in which one side thereof is coated with the stretchable film 1 is removed temporarily (FIG. 4A) from the substrate 2 of the coated wiring substrate 7 produced by the method shown in FIGS. 3A to 3E. Then, this was put on the substrate 2, with the coated surface (i.e., the side of the stretchable film 1) being downward (FIG. 4B). Subsequently, this is coated with the composition which contains the components (A) to (C) described above to form the coating film 3 of the composition (FIG. 4C). Then, the component (C) is evaporated by heating, while localizing the component (A) in the direction of the surface of the film to form the coated film 4 in which the component (A) is localized (FIG. 4D). Subsequently, the component (A) and the component (B) are cured by light irradiation to form the stretchable film 1 (FIG. 4E). This allows manufacturing of the stretchable wiring film 6 in which the both sides of the conductive wiring 5 are coated with the stretchable films 1 (FIG. 4F).

Such a manufacturing method, coating the both sides of a conductive wiring with the inventive stretchable films, makes it possible to easily manufacture a stretchable wiring film that is also excellent in repellency on the surface not only excellent in stretchability and strength.

It is to be noted that the inventive method for manufacturing a stretchable wiring film may be a method for manufacturing a stretchable wiring film in which a conductive wiring having stretchability is sandwiched between two of the inventive stretchable films on the both sides thereof to locate each stretchable film such that the surface where the component (A) is localized faces outside, and this is laminated by heating and pressing, thereby coating the both sides of the conductive wiring.

The conductive wiring having stretchability used herein can be the same ones mentioned in the explanation of the stretchable wiring film described above.

Figure 5A:
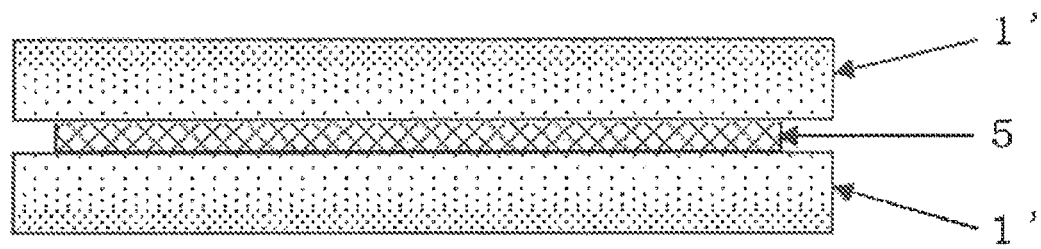
FIGS. 5A to 5C are a flow diagram showing another example of the inventive method for manufacturing a stretchable wiring film.
Figure 5B:
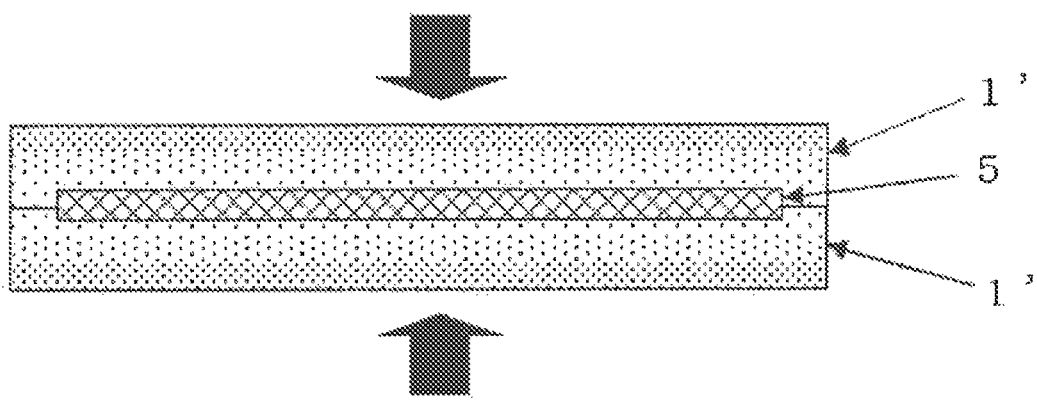
Figure 5C:
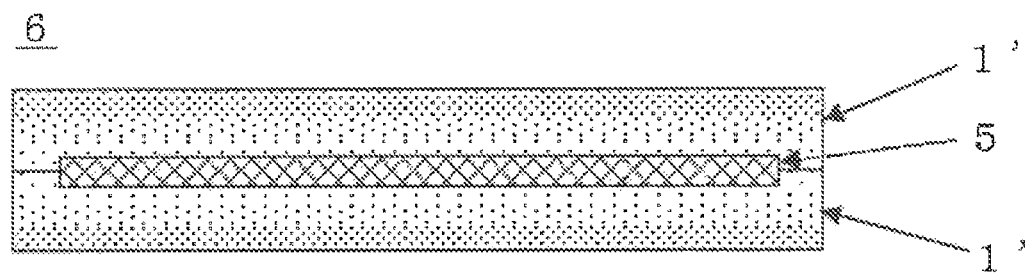

A flow diagram of FIGS. 5A to 5C shows another example of the inventive method for manufacturing a stretchable wiring film. In the method shown in FIGS. 5A to 5C, the conductive wiring 5 having stretchability is sandwiched at first between two of the stretchable films 1' on the both sides thereof to locate each stretchable film 1' such that the surface where the component (A) is localized faces outside (FIG. 5A). Then, this is laminated by heating and pressing (FIG. 5B). This allows manufacturing of the stretchable wiring film 6 in which the both sides of the conductive wiring 5 are coated with the stretchable films 1' (FIG. 5C).

Figure 6A:
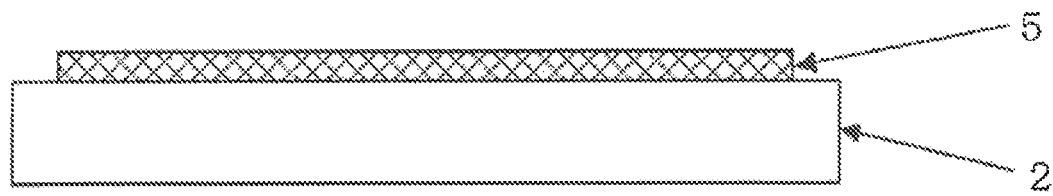
FIGS. 6A to 6D are a flow diagram showing still another example of the inventive method for manufacturing a stretchable wiring film.
Figure 6B:
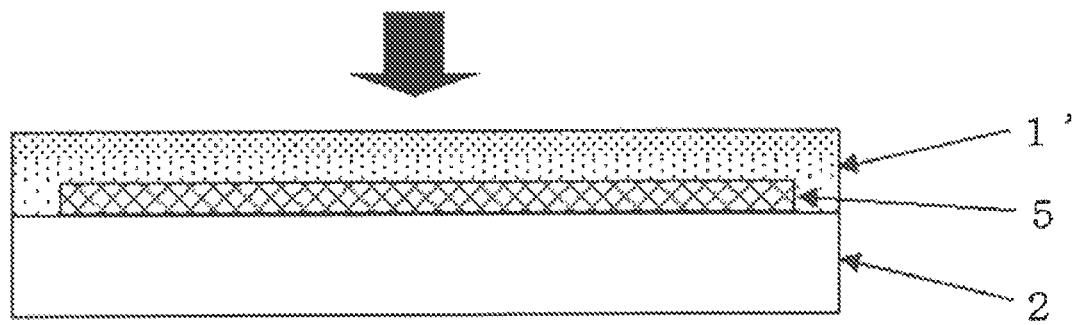
Figure 6C:
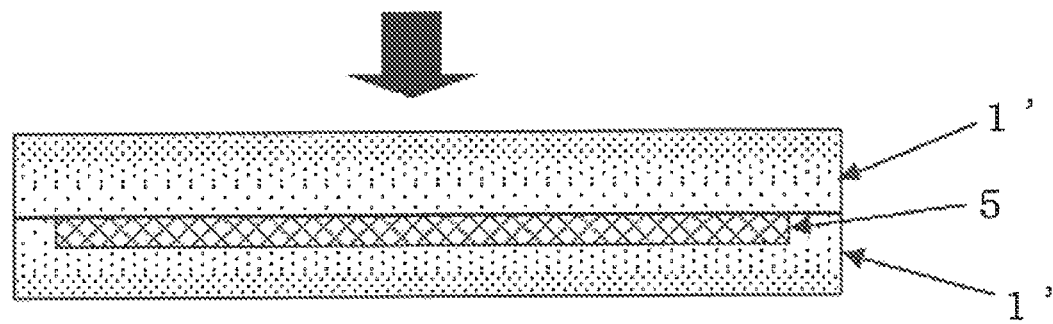
Figure 6D:
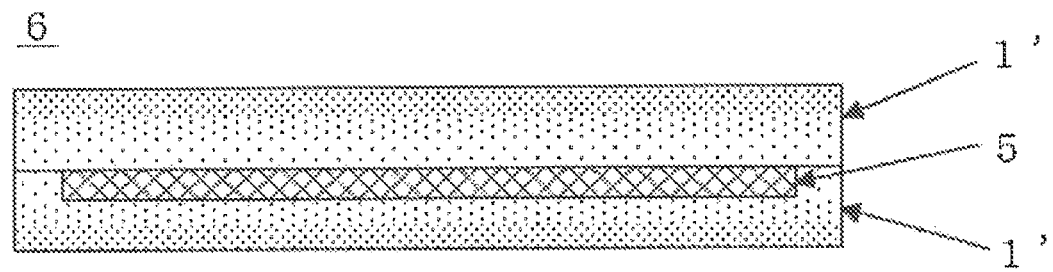

Moreover, the inventive method for manufacturing a stretchable wiring film may be such a method as shown in FIGS. 6A to 6D. In the method shown in FIGS. 6A to 6D, the conductive wiring 5 having stretchability is placed on the substrate 2 at first (FIG. 6A). Then, the stretchable film 1' is laminated onto one side of the conductive wiring 5 by heating and pressing such that the surface where the component (A) is localized faces outside (FIG. 6B). After delaminating the substrate 2, the stretchable film 1' is laminated onto the opposite side of the conductive wiring 5 by heating and pressing such that the surface where the component (A) is localized faces outside (FIG. 6C). This allows manufacturing of the stretchable wiring film 6 in which the both sides of the conductive wiring 5 are coated with the stretchable films 1' (FIG. 6D).

Although this method can manufacture a stretchable wiring film easily through lamination using the inventive stretchable film, the method shown in the foregoing FIGS. 5A to 5C is more preferable. Since the latter method can perform the laminate processing of FIG. 6B and FIG. 6C at once to simplify the lamination step.

Lamination is a convenient method for coating a main material with film shaped resin fitted to the shape of the main material by heating and pressing, and is used in many fields. With a film formed from silicone resin only, it has been unsuccessful to form an unsupported film due to its lower strength. In the inventive stretchable film, however, most of the film component can be composed of urethane resin (the component (B)) having higher strength and stretchability, with the slight portion at the surface being composed of silsesquioxane resin (the component (A)), which allows the film to have excellent strength equal to that of urethane resin. Accordingly, this film can be delaminated from a substrate to be an unsupported film, and can be applied to laminate processing.

The temperature at the laminate processing is preferably about 50 to 150° C. though it is not particularly limited, and the pressure at the laminate processing is preferably about 0.1 to 10 kg/cm² though it is not particularly limited.

EXAMPLES

Hereinafter, the present invention will be specifically described with reference to Examples and Comparative Examples, but the present invention is not limited thereto. Incidentally, the weight average molecular weight (Mw) represents a weight average molecular weight in terms of polystyrene determined by gel permeation chromatography (GPC).

The following are Silsesquioxane-(meth)acrylates-1 to 5 each blended to a composition for forming a stretchable film as the component (A).

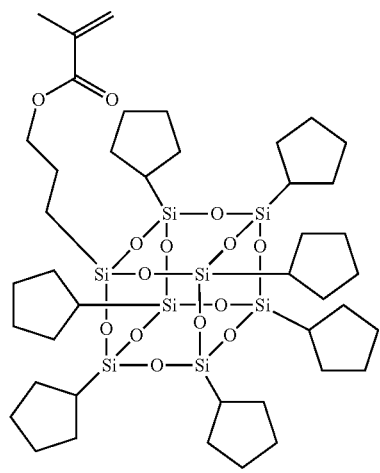

Silsequioxane-(meth) acrylate-1

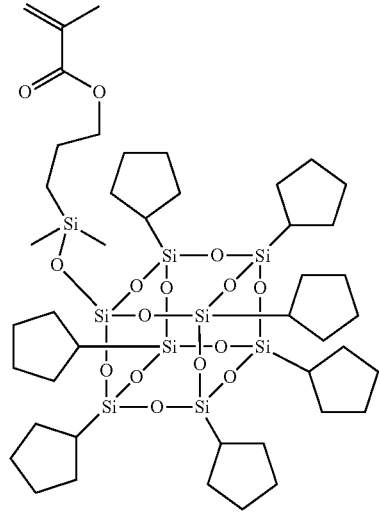

Silsequioxane-(meth) acrylate-2

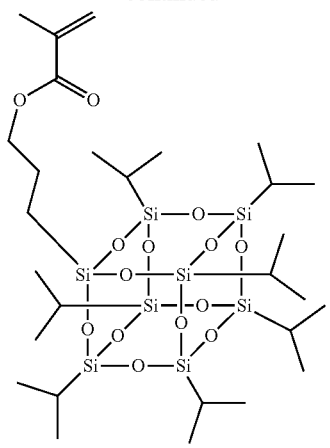

Silsequioxane-(meth) acrylate-3

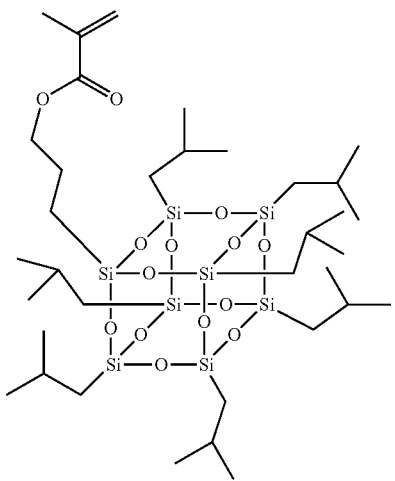

Silsequioxane-(meth) acrylate-4

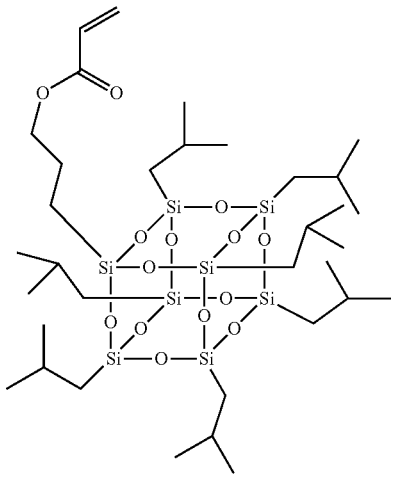

Silsequioxane-(meth) acrylate-5

The following are Urethane-acrylates-1 to 11 and Silicone-acrylate-1 each blended to a composition for forming a stretchable film as the component (B).

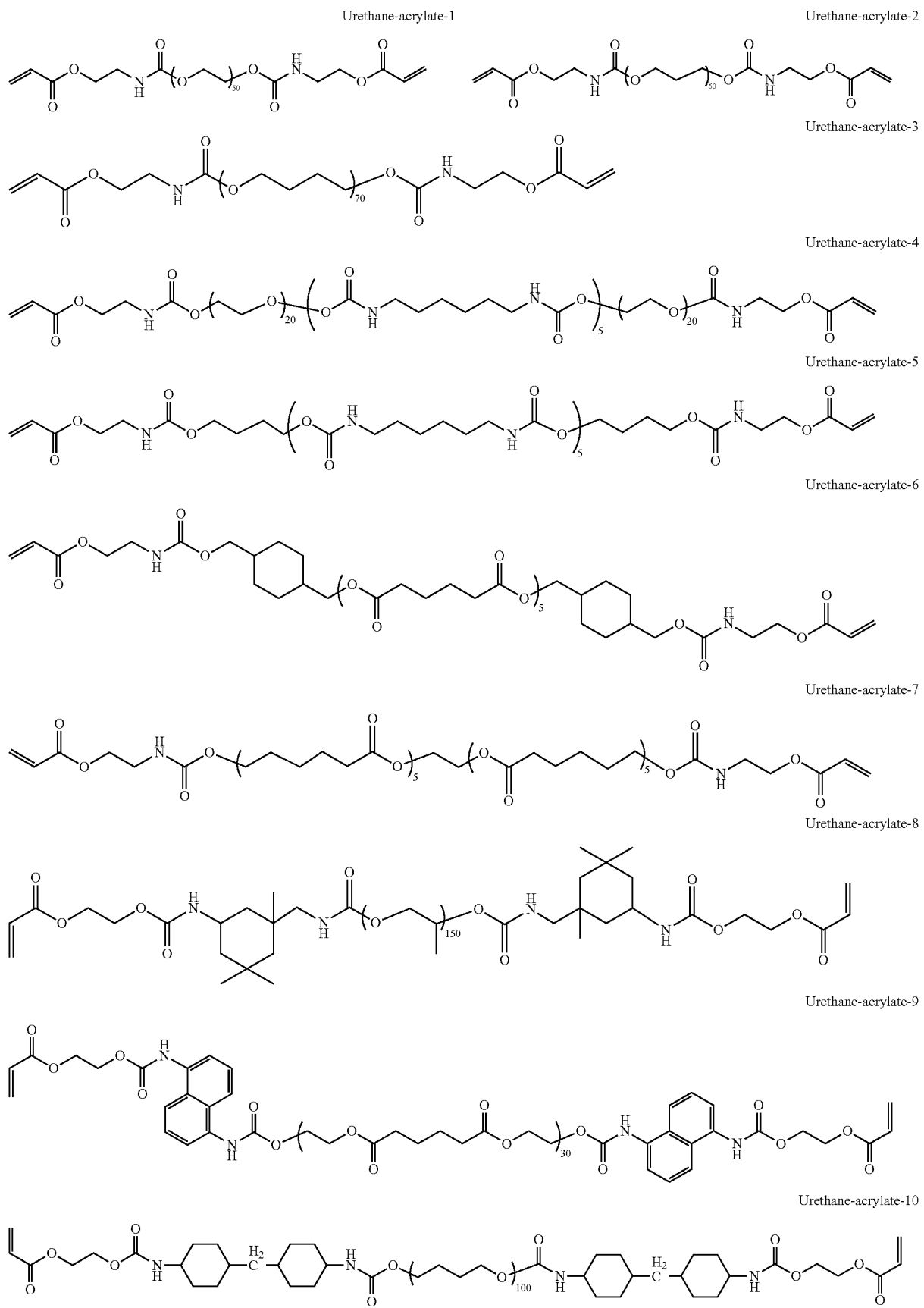

-continued

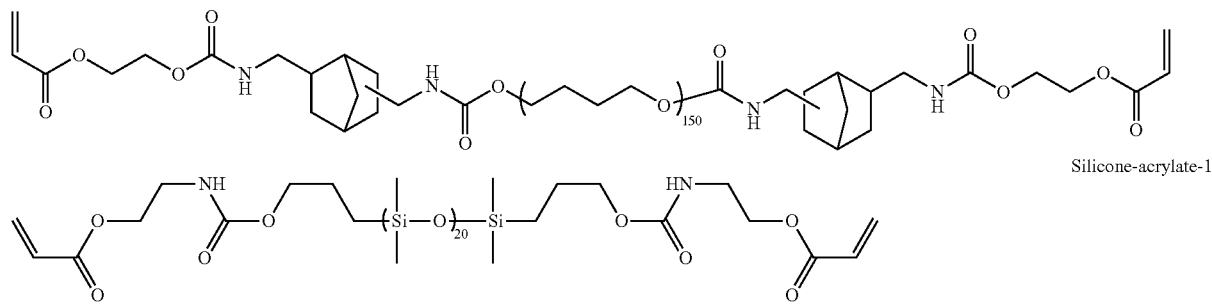

Urethane-acrylate-11

Silicone-acrylate-1

In the foregoing formulae, the numbers of repeating units are average values.

The following are Photo-radical generators-1 to 4 and Thermal radical generators-1 and 2 each blended to a composition for forming a stretchable film as an additive.
Photo-radical generator-1: 4,4'-dimethoxybenzyl
Photo-radical generator-2: 2,2-diethoxyacetophenone
Photo-radical generator-3: 2,2-dimethoxy-2-phenylacetophenone
Photo-radical generator-4: (±)-camphorquinone
Thermal radical generator-1: dimethyl 2,2'-azobis(2-methylpropionate)
Thermal radical generator-2: azobis(isobutyronitrile) (AIBN)

The following are boiling points at atmospheric pressure of organic solvents each blended to a composition for forming a stretchable film as the component (C) or the replacements.
2-heptanone: 151° C.
2-octanone: 173° C.
cyclohexanone: 156° C.
amyl acetate: 149° C.
isoamyl acetate: 142° C.
butyl acetate: 126° C.
PGMEA (propylene glycol monomethyl ether acetate): 146° C.
PGME (propylene glycol monomethyl ether): 120° C. ethanol: 78° C.
2-ethylhexyl acrylate: 214° C.
1-vinyl-2-pyrrolidone: 90° C.

Examples 1 to 16 and Comparative Examples 1 to 4

Silsesquioxane-(meth)acrylates-1 to 5, Urethane-acrylates-1 to 11, Silicone-acrylate-1, Photo-radical generators-1 to 4, Thermal radical generators-1 and 2, and organic solvents were blended in each formulation described in Tables 1 and 2 to prepare compositions for forming a stretchable film (Sols-1 to 16, Comparative Sols-1 to 4). Onto a substrate with the surface being coated with Teflon (registered trade mark), each prepared compositions for forming a stretchable film was applied by bar coating method. This was baked at 110° C. for 20 minutes in each case of Sols-1 to 14 and Comparative Sols-1 to 4, and then irradiated with 1 J/cm² of light with a 1,000 W xenon lamp in a nitrogen atmosphere, thereby curing the coating film of the composition to form a stretchable film (each of Films-1 to 14, Comparative Films-1 to 4) with the thickness of 100 μm on the substrate. In each case of Sols-15 and 16, the prepared compositions for forming a stretchable film was applied by bar coating method onto a substrate with the surface being coated with Teflon (registered trade mark), and baked at 110° C. for 20 minutes in a nitrogen atmosphere.

TABLE 1

| Composition * | Component (A) (parts by mass) | Component (B) (parts by mass) | Additives (parts by mass) | Organic solvent (parts by mass) |
|---|---|---|---|---|
| Sol-1 | Silsesquioxane-(meth) acrylate-1 (7) | Urethane-acrylate-1 (93) | Photo-radical generator-1 (3.0) | 2-heptanone (30) |
| Sol-2 | Silsesquioxane-(meth) acrylate-2 (8) | Urethane-acrylate-2 (92) | Photo-radical generator-2 (3.0) | 2-heptanone (30) |
| Sol-3 | Silsesquioxane-(meth) acrylate-3 (10) | Urethane-acrylate-3 (90) | Photo-radical generator-3 (3.0) | 2-heptanone (30) |
| Sol-4 | Silsesquioxane-(meth) acrylate-4 (10) | Urethane-acrylate-4 (90) | Photo-radical generator-3 (3.0) | 2-heptanone (30) |
| Sol-5 | Silsesquioxane-(meth) acrylate-1 (10) | Urethane-acrylate-5 (90) | Photo-radical generator-3 (3.0) | cyclohexanone (30) |
| Sol-6 | Silsesquioxane-(meth) acrylate-5 (10) | Urethane-acrylate-6 (90) | Photo-radical generator-3 (3.0) | amyl acetate (30) |
| Sol-7 | Silsesquioxane-(meth) acrylate-1 (20) | Urethane-acrylate-7 (80) | Photo-radical generator-3 (3.0) | PGMEA (30) |
| Sol-8 | Silsesquioxane-(meth) acrylate-1 (2) Silsesquioxane-(meth) acrylate-2 (6) | Urethane-acrylate-8 (90) | Photo-radical generator-3 (3.0) | isoamyl acetate (30) |
| Sol-9 | Silsesquioxane-(meth) acrylate-1 (15) | Urethane-acrylate-9 (85) | Photo-radical generator-3 (3.0) | 2-heptanone (20) butyl acetate (10) |
| Sol-10 | Silsesquioxane-(meth) acrylate-1 (4) | Urethane-acrylate-10 (96) | Photo-radical generator-3 (3.0) | 2-octanone (15) PGME (15) |

TABLE 1-continued

| Composition * | Component (A) (parts by mass) | Component (B) (parts by mass) | Additives (parts by mass) | Organic solvent (parts by mass) |
|---|---|---|---|---|
| Sol-11 | Silsesquioxane-(meth) acrylate-1 (5) | Urethane-acrylate-11 (95) | Photo-radical generator-3 (3.0) | PGMEA (30) |
| Sol-12 | Silsesquioxane-(meth) acrylate-1 (10) | Urethane-acrylate-1 (60) Urethane-acrylate-11 (30) | Photo-radical generator-3 (3.0) | PGMEA (30) |
| Sol-13 | Silsesquioxane-(meth) acrylate-1 (5) | Urethane-acrylate-11 (95) | Photo-radical generator-3 (3.0) | PGMEA (30) |
| Sol-14 | Silsesquioxane-(meth) acrylate-1 (5) | Urethane-acrylate-11 (95) | Photo-radical generator-4 (2.5) | PGMEA (30) |
| Sol-15 | Silsesquioxane-(meth) acrylate-1 (7) | Urethane-acrylate-1 (93) | Thermal radical generator-1 (3.2) | 2-heptanone (30) |
| Sol-16 | Silsesquioxane-(meth) acrylate-1 (7) | Urethane-acrylate-1 (93) | Thermal radical generator-2 (3.8) | 2-heptanone (30) |

* composition for forming a stretchable film

TABLE 2

| Composition* | Component (A) (parts by mass) | Component (B) (parts by mass) | Additives (parts by mass) | Organic solvent (parts by mass) |
|---|---|---|---|---|
| Comparative Sol-1 | — | Silicone-acrylate-1 (100) | Photo-radical generator-3 (3.0) | 2-heptanone (30) |
| Comparative Sol-2 | — | Urethane-acrylate-1 (100) | Photo-radical generator-3 (3.0) | 2-heptanone (30) |
| Comparative Sol-3 | — | Silicone-acrylate-1 (10) Urethane-acrylate-1 (90) | Photo-radical generator-3 (3.0) | ethanol (100) |
| Comparative Sol-4 | — | Silicone-acrylate-1 (10) Urethane-acrylate-1 (90) | Photo-radical generator-3 (3.0) | 2-ethylhexyl acrylate (50), 1-vinyl-2-pyrrolidone (50) |

*composition for forming a stretchable film (Measurement of Contact Angle, Stretching Property, and Strength)

The contact angle with water was measured on the surface of each stretchable film after curing. After measuring the contact angle with water on the surface of the stretchable film, the stretchable film was removed from the substrate, and subjected to measurement of the stretching property and strength in conformity to JIS K 6251. The results are shown in Table 3.

TABLE 3

| | Stretchable film | Composition for forming a stretchable film | Contact angle (°) | Stretching property (%) | Strength (kgf/cm²) |
|---|---|---|---|---|---|
| Example 1 | Film-1 | Sol-1 | 83 | 130 | 68 |
| Example 2 | Film-2 | Sol-2 | 84 | 123 | 68 |
| Example 3 | Film-3 | Sol-3 | 88 | 152 | 50 |
| Example 4 | Film-4 | Sol-4 | 84 | 150 | 92 |
| Example 5 | Film-5 | Sol-5 | 85 | 110 | 99 |
| Example 6 | Film-6 | Sol-6 | 93 | 120 | 93 |
| Example 7 | Film-7 | Sol-7 | 82 | 150 | 99 |
| Example 8 | Film-8 | Sol-8 | 84 | 160 | 88 |
| Example 9 | Film-9 | Sol-9 | 83 | 150 | 93 |
| Example 10 | Film-10 | Sol-10 | 86 | 177 | 95 |
| Example 11 | Film-11 | Sol-11 | 85 | 166 | 97 |
| Example 12 | Film-12 | Sol-12 | 90 | 140 | 81 |
| Example 13 | Film-13 | Sol-13 | 88 | 120 | 88 |
| Example 14 | Film-14 | Sol-14 | 83 | 155 | 92 |
| Example 15 | Film-15 | Sol-15 | 94 | 133 | 155 |
| Example 16 | Film-16 | Sol-16 | 98 | 168 | 122 |
| Comparative Example 1 | Comparative Film-1 | Comparative Sol-1 | 71 | — | — |
| Comparative Example 2 | Comparative Film-2 | Comparative Sol-2 | 50 | 85 | 80 |
| Comparative Example 3 | Comparative Film-3 | Comparative Sol-3 | 54 | 83 | 70 |
| Comparative Example 4 | Comparative Film-4 | Comparative Sol-4 | 55 | 75 | 72 |

In Examples 1 to 16, the obtained stretchable films (Films-1 to 16) each had excellent stretchability and strength, together with excellent repellency on the film surface as shown in Table 3 since the component (A) was localized in the direction of film surface by baking after forming the coating film of the composition while evaporating the component (C), and the component (A) and the component (B) were cured by light irradiation or heat in this state by using each of the compositions for forming a stretchable film (Sols-1 to 16) that contained Silsesquioxane-(meth)acrylates-1 to 5 (the component (A)), Urethane-acrylates-1 to 11 (the component (B)), and the organic solvents each having a boiling point in the range of 115 to 200° C. at atmospheric pressure (the component (C)) to form the stretchable film.

On the other hand, the stretchable film (Comparative Film-1) in Comparative Example 1 showed lower repellency, stretchability, and strength by using the composition for forming a stretchable film (Comparative Sol-1) that contained Silicone-acrylate-1 as the component (B) without containing a component (A), and the stretching property and strength could not be measured. In comparative Example 2, the stretchable film (Comparative Film-2) was inferior in repellency as well as stretchability and strength to Examples 1 to 16 since the component (A) was not contained in the film, which was formed by using the composition for forming a stretchable film (Comparative Sol-2) that contained Urethane-acrylate-1 as the component (B) without containing a component (A). In Comparative Examples 3 and 4, the stretchable films (Comparative Films-3 and 4) were inferior in repellency, stretchability, and strength to those in Examples 1 to 16 by using each composition for forming a stretchable film (Comparative Sols-3 or 4) that contained an organic solvent with the boiling point of below 115° C. or above 200° C. at atmospheric pressure instead of the component (C) without containing a component (A).

As described above, it has revealed that the inventive stretchable film is excellent in stretchability and strength as well as repellency on the film surface, thereby having excellent properties as a film to coat a stretchable wiring used for a wearable device, etc.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A stretchable film comprising:
   a cured product of a composition which contains (A) a (meth)acrylate compound having silsesquioxane, (B) a (meth)acrylate compound other than the component (A) having a urethane bond, and (C) an organic solvent having a boiling point in the range of 115 to 200° C. at atmospheric pressure;
   wherein the component (A) is localized in the direction of a surface of the film,
   wherein the component (B) is a compound shown by the following general formula (3), and the composition is one without a polymerizable double bond other than the component (A) and the component (B):

wherein the component (A) is a compound shown by the following general formula (1):

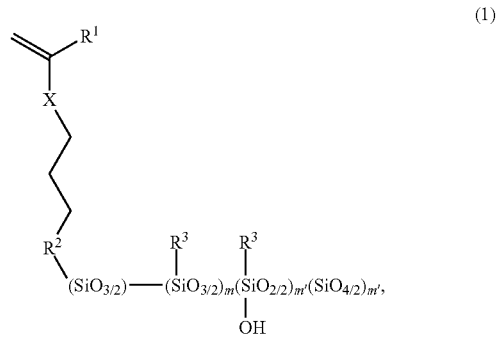

wherein $R^1$ represents a hydrogen atom or a methyl group; $R^2$ represents a single bond or a linking group shown by the following general formula (2); each $R^3$ is the same or different, and represents a hydrogen atom, a hydroxy group, or a linear, branched, or cyclic hydrocarbon group having 1 to 10 carbon atoms, optionally containing an ether group, a lactone group, an ester group, a hydroxy group, or a cyano group; X represents an ester group or —C(=O)—O—$R^7$—; $R^7$ represents a linear, branched, or cyclic alkylene group having 1 to 14 carbon atoms, a linear, branched, or cyclic alkenylene group or alkynylene group having 2 to 14 carbon atoms, or an arylene group having 6 to 10 carbon atoms, optionally having an ether group or an ester group; "m" is an integer of 4 to 40, "m'" is 0 or 1, "m''" is an integer of 0 to 8; and a part of a siloxane bond in the ($R^3$—SiO$_{3/2}$)$_m$ unit is optionally cut to form a silanol group;

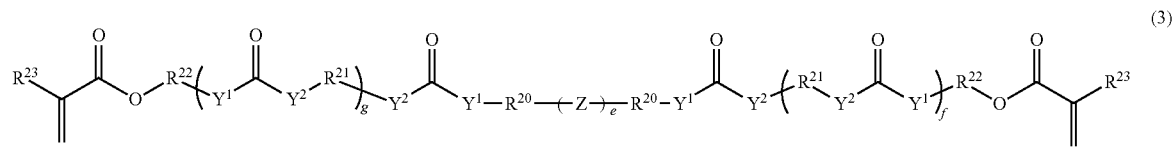

wherein $R^{23}$ represents a hydrogen atom or a methyl group; $R^{20}$ and $R^{22}$ each independently represent a single bond, a linear, branched, or cyclic alkylene group having 1 to 20 carbon atoms, an arylene group having 6 to 20 carbon atoms, or an alkenylene group having 2 to 20 carbon atoms, optionally having one or more group selected from an ether group, an ester group, an aryl group, and an arylene group; $R^{21}$ represents a single bond or a divalent hydrocarbon group having 1 to 15 carbon atoms; Z represents a single bond or a divalent hydrocarbon group having 1 to 12 carbon atoms, optionally containing one or more group selected from an ether group, an ester group, and a carbonate group; one of $Y^1$ and $Y^2$ represents an oxygen atom, and the other represents a NH group; "e" is an integer of 1 to 100, "f" is an integer of 0 to 200, and "g" is an integer of 0 to 200, and

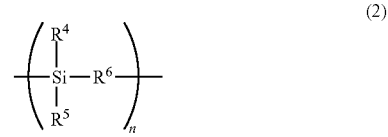

wherein $R^4$ and $R^5$ each independently represent a linear, branched, or cyclic alkyl group having 1 to 10 carbon atoms; $R^6$ represents a single bond, an oxygen atom, or an alkylene group having 1 to 4 carbon atoms; and "n" is an integer of 1 to 40.

2. The stretchable film according to claim 1, wherein the ratio of the component (A) is in the range of 0.1 to 35% by mass based on the total mass of solid contents in the composition excluding the component (C).

3. The stretchable film according to claim 1, wherein the component (C) is one or more organic solvents selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, propylene glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, and propylene glycol monoethyl ether acetate.

4. The stretchable film according to claim 1, wherein the stretchable film has a stretching property of 40 to 600% regulated by JIS K 6251.

5. A stretchable conductive wiring film comprising the stretchable film according to claim 1.

6. A method for forming a stretchable film of claim 1 comprising:
coating a substrate with a composition which contains (A) a (meth)acrylate compound having silsesquioxane, (B) a (meth)acrylate compound other than the component (A) having a urethane bond, and (C) an organic solvent having a boiling point in the range of 115 to 200° C. at atmospheric pressure;
evaporating the component (C) by heating, while localizing the component (A) in the direction of a surface of the film; and thereafter
curing the component (A) and the component (B) by heat or light irradiation.

7. The method for forming a stretchable film according to claim 6, wherein the ratio of the component (A) is in the range of 0.1 to 35% by mass based on the total mass of solid contents in the composition excluding the component (C).

8. The method for forming a stretchable film according to claim 6, wherein the component (A) is a compound shown by the following general formula (1):

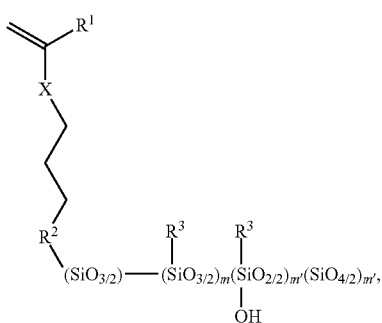

(1)

wherein $R^1$ represents a hydrogen atom or a methyl group; $R^2$ represents a single bond or a linking group shown by the following general formula (2); each $R^3$ is the same or different, and represents a hydrogen atom, a hydroxy group, a linear, branched, or cyclic hydrocarbon group having 1 to 10 carbon atoms, or a fluorinated alkyl group, optionally containing an ether group, a lactone group, an ester group, a hydroxy group, or a cyano group; X represents an ester group or $-C(=O)-O-R^7-$; $R^7$ represents a linear, branched, or cyclic alkylene group having 1 to 14 carbon atoms, a linear, branched, or cyclic alkenylene group or alkynylene group having 2 to 14 carbon atoms, or an arylene group having 6 to 10 carbon atoms, optionally having an ether group or an ester group; "m" is an integer of 4 to 40, "m'" is 0 or 1, "m''" is an integer of 0 to 8; and a part of a siloxane bond in the $(R^3-SiO_{3/2})_m$ unit is optionally cut to form a silanol group;

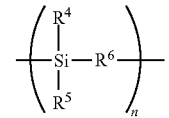

(2)

wherein $R^4$ and $R^5$ each independently represent a linear, branched, or cyclic alkyl group having 1 to 10 carbon atoms; $R^6$ represents a single bond, an oxygen atom, or an alkylene group having 1 to 4 carbon atoms; and "n" is an integer of 1 to 40.

9. The method for forming a stretchable film according to claim 7, wherein the component (A) is a compound shown by the following general formula (1):

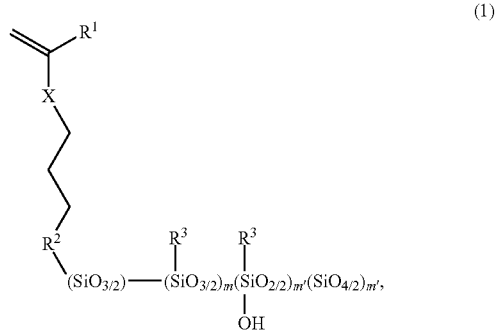

(1)

wherein $R^1$ represents a hydrogen atom or a methyl group; $R^2$ represents a single bond or a linking group shown by the following general formula (2); each $R^3$ is the same or different, and represents a hydrogen atom, a hydroxy group, a linear, branched, or cyclic hydrocarbon group having 1 to 10 carbon atoms, or a fluorinated alkyl group, optionally containing an ether group, a lactone group, an ester group, a hydroxy group, or a cyano group; X represents an ester group or $-C(=O)-O-R^7-$; $R^7$ represents a linear, branched, or cyclic alkylene group having 1 to 14 carbon atoms, a linear, branched, or cyclic alkenylene group or alkynylene group having 2 to 14 carbon atoms, or an arylene group having 6 to 10 carbon atoms, optionally having an ether group or an ester group; "m" is an integer of 4 to 40, "m'" is 0 or 1, "m''" is an integer of 0 to 8; and a part of a siloxane bond in the $(R^3-SiO_{3/2})_m$ unit is optionally cut to form a silanol group;

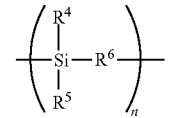

(2)

wherein $R^4$ and $R^5$ each independently represent a linear, branched, or cyclic alkyl group having 1 to 10 carbon atoms; $R^6$ represents a single bond, an oxygen atom, or an alkylene group having 1 to 4 carbon atoms; and "n" is an integer of 1 to 40.

10. The method for forming a stretchable film according to claim 6, wherein the component (B) is a compound shown by the following general formula (3):

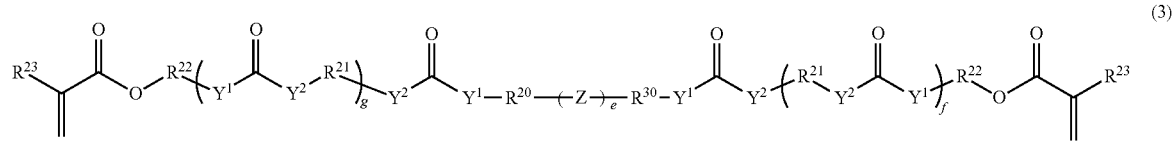

(3)

wherein $R^{23}$ represents a hydrogen atom or a methyl group; $R^{20}$ and $R^{22}$ each independently represent a single bond, a linear, branched, or cyclic alkylene group having 1 to 20 carbon atoms, an arylene group having 6 to 20 carbon atoms, or an alkenylene group having 2 to 20 carbon atoms, optionally having one or more group selected from an ether group, an ester group, an aryl group, and an arylene group; $R^{21}$ represents a single bond or a divalent hydrocarbon group having 1 to 15 carbon atoms; Z represents a single bond or a divalent hydrocarbon group having 1 to 12 carbon atoms, optionally containing one or more group selected from an ether group, an ester group, and a carbonate group; one of $Y^1$ and $Y^2$ represents an oxygen atom, and the other represents a NH group; "e" is an integer of 1 to 100, "f" is an integer of 0 to 200, and "g" is an integer of 0 to 200.

11. The method for forming a stretchable film according to claim 6, wherein the component (C) is one or more organic solvents selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, propylene glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, and propylene glycol monoethyl ether acetate.

12. A stretchable wiring film, comprising a conductive wiring having stretchability, the both sides of the conductive wiring being coated with the stretchable film according to claim 1; wherein the surface localizing the component (A) of the stretchable film is disposed on the outside, and the conductive wiring is disposed on the inside.

13. A method for manufacturing a stretchable wiring film according to claim 12, comprising:
putting the conductive wiring having stretchability onto a substrate;
coating the substrate having the conductive wiring thereon with the composition which contains the component (A), the component (B), and the component (C);
evaporating the component (C) by heating, while localizing the component (A) in the direction of a surface of the film; and thereafter
curing the component (A) and the component (B) by heat or light irradiation to form a stretchable film, thereby producing a coated wiring substrate having a single-side-coated conductive wiring;
removing the single-side-coated conductive wiring temporarily from the substrate of the coated wiring substrate;
putting the single-side-coated conductive wiring onto the substrate, with the coated side being downward;
coating the substrate having the single-side-coated conductive wiring thereon with the composition which contains the component (A), the component (B), and the component (C);
evaporating the component (C) by heating, while localizing the component (A) in the direction of a surface of the film; and thereafter
curing the component (A) and the component (B) by heat or light irradiation to produce a stretchable wiring film in which both sides of the conductive wiring are coated.

* * * * *